United States Patent [19]

Sachinvala et al.

[11] Patent Number: 5,789,469
[45] Date of Patent: Aug. 4, 1998

[54] POLYMERS HAVING ENHANCED THERMAL STABILITIES AND METHODS FOR THEIR PREPARATION USING STABILIZATION AGENTS 1,6,6'-TRIMETHACRYLOYL 2,3,3',4,4'-PENTA-O-METHYLSUCROSE 1',2,3,3',4,4',6,6'-OCTA-O-ALLYLSUCROSE 1',2,3,3',4,4',6,6'-OCTO-O-CROTYLSUCROSE

[75] Inventors: Navzer D. Sachinvala; Redford Fu Ju, both of Aiea, Hi.; Morton H. Litt, Cleveland, Ohio

[73] Assignees: Hawaii Agriculture Research Center, Aiea, Hi.; The United States of America as represented by the Department of Agriculture—Agricultural Research Center, Washington, D.C.

[21] Appl. No.: 923,112

[22] Filed: Sep. 4, 1997

Related U.S. Application Data

[63] Continuation of Ser. No. 605,643, Feb. 22, 1996, which is a continuation of Ser. No. 468,315, Jun. 6, 1995, which is a division of Ser. No. 199,695, Feb. 28, 1994, Pat. No. 5,470,931, which is a continuation-in-part of Ser. No. 28,545, Mar. 8, 1993, abandoned, which is a continuation-in-part of Ser. No. 877,813, May 4, 1992, Pat. No. 5,248,747, which is a continuation-in-part of Ser. No. 697,983, May 10, 1991, Pat. No. 5,116,961, which is a continuation-in-part of Ser. No. 623,548, Dec. 7, 1990, abandoned.

[51] Int. Cl.$^6$ ..................................... C08K 5/15
[52] U.S. Cl. .................. 524/56; 524/732; 524/369; 524/755; 524/560; 524/555; 524/565; 524/577
[58] Field of Search ..................... 524/369, 755, 524/56, 732; 526/209, 200, 238.23

[56] References Cited

U.S. PATENT DOCUMENTS

| | | | |
|---|---|---|---|
| 2,492,169 | 12/1949 | Mast et al. | 525/354 |
| 2,539,706 | 1/1951 | Snyder | 526/216 |
| 2,606,881 | 8/1952 | Zief et al. | 526/238.21 |
| 2,687,430 | 8/1954 | Snow et al. | 560/254 |
| 2,702,825 | 2/1955 | Ross et al. | 568/663 |
| 3,915,921 | 10/1975 | Schlatzer, Jr. | 526/238.23 |
| 3,978,022 | 8/1976 | Carson | 524/392 |
| 4,048,426 | 9/1977 | Solomon | 526/334 |
| 4,119,612 | 10/1978 | Vollkommer et al. | 528/232 |
| 4,587,319 | 5/1986 | Tournier | 527/313 |
| 5,116,961 | 5/1992 | Sachinvala et al. | 536/18.2 |
| 5,248,747 | 9/1993 | Sachinvala et al. | 526/238.23 |
| 5,302,676 | 4/1994 | Sachinvala et al. | 526/238.23 |

FOREIGN PATENT DOCUMENTS

| | | |
|---|---|---|
| 03045604A2 | 2/1991 | Japan . |
| 0537660 | 4/1993 | Japan . |

OTHER PUBLICATIONS

G R Ames Chem Rev 60, 541 (1960).
CA 104 (18): 150001f (Paus 1986).
CA 70 (16): 68960p (Shafranskaya 1968).
LM Novichkou, Izvestiya Acad Sci. Kaz Sov. Soc. Rep. Chem. Ser. (1987) , (6), 68–73.
A H Conner et al., Adhesives from Renewable Resources. Hemmingway et al., eds., Am. Chem. Soc. (1989) 355–369.
A W Christiansen et al., Adhesives from Renewable Resources, Hemmingway et al., eds., Am Chem Soc (1989) 370–386.
J. March, Advanced Organic Chemistry, 4th Ed., Wiley, New York, 1992, 389–90.
I.C. McNeill, Comprehensive Polymer Science, I.C. McNeil, Ed., vol. 6, Pergamon Press, New York, pp. 451–500, 1989.
N. Grassie, Chemistry of High Polymer Degradation Processes, Interscience Publishers Inc., New York, 1956.
N. Grassie, A. Scotney, R. Jenkins, and T.I. Davis, Chem. zvesti, 26, 208 (1972).
N. Grassie and G. Scott, Polymer Degradation & Sabilisation, Cambridge University Press, London, pp. 1–67, 1985.
D.H. Solomon, J. Macromol. Sci. Chem.,A17, 337 (1992).
N. Grassie, Pure & Appl. Chem., 30, 119 (1972).
N. Grassie and .W. Melville, Proc. Royal Soc. London., A199, 14 (1949).
K.A. Holland and I.D. Rae, Aust. J. Chem., 40, 687 (1987).
A. Meisters, G. Moad, E. Rizzardo, and D.H. Solomon, Poly, Bull. 20, 499 (1988).
T. Kashiwagi, A. Omori, and H. Nanbu, Combustion and Flame, 81, 188 (1990).
T. Kashiwagi, A. Inaba, J.E. Brown, K. Hatada, T. Kitayama and E. Masuda, Macromolecules, 19, 2160 (1986).
N. Grassie, A. Johnston, and A. Sctoney, Eur. Polym. J., 17, 589 (1981).
N. Grassie, M.A.M. Diab, and A. Scotney, Polym. Degradation Stab., 16, 19 (1986).

(List continued on next page.)

Primary Examiner—Mark Nagumo
Attorney, Agent, or Firm—Burns, Doane, Swecker & Mathis, L.L.P.

[57] ABSTRACT

A method for producing stabilized polymers, exhibiting enhanced thermal stability, which comprises polymerizing a mixture comprising: a monomer comprising an allyl-containing group which is bonded to primary and/or secondary hydroxyl groups on a saccharide, preferably a long chain ($C_3$–$C_{20}$) allyl-containing ether group on the hydroxyl group; and one or monomers selected from methacrylate ester monomers, acrylate ester monomers, acrylamide monomers and styrene monomers, in amounts sufficient to produce a polymer exhibiting enhanced thermal stability. Polymers having enhanced thermal stability are obtained using a monomer comprising an allyl-containing group which is bonded to primary and/or secondary hydroxyl groups on a saccharide, as a novel stabilization crosslinking agent. In addition, a method of using non-crosslinking sucrose-based monomers, preferably having a methyl, alkyl or crotyl ether on at least one of the hydroxyl groups of sucrose, in polymerization processes, and non-crosslinked polymers having enhanced thermal stability obtained using these non-crosslinking sucrose-based additives are provided.

9 Claims, 5 Drawing Sheets

OTHER PUBLICATIONS

J. Popovic, Ch–H Song, L. Fischer, L. Katsikas, G. Hohne, J. Velickovic, and W. Schnabel, *Polym. Degradation Stab.*, 31, 265 (1991).

K. Hayakawa, K. Kawase, and H. Yamakita, *J. Appl. Polym. Sci.*, 29, 4061 (1984).

J. San Roman, E.L. Madruga, and Y. J. Fontan, *Rev. Plast. Mod.*, 31, 213 (1976).

V.S. Nikiforenko, Yu S. Zaitsev, N.N. Alekseev, and O.I. Sholgon, *Plast. Massy*, 59, (1988).

F.M. Aliev and V. N. Zgonik, *Euro. Polym. J.*, 27, 969 (1991).

H.H.G. Jellinek, *Degradation of Vinyl Polymers*, Academic Press, New York, 74 1965.

I.C. McNeil, *Eur. Polym. J.*, 4,21 (1968).

P. Cacioli, G. Moad, E. Rizzardo, A.K. Serelis and D.H. Solomon, *Polym. Bull. (Berlin)*, 11, 325 (1984).

A. Kaminska, H. Kacmaerk, and S. Sanyal, *Polym. Networks Blends*, 1, 165 (1991).

A. Rincon, I.C. McNeil, *Polym. Degradation and Stab.*, 18, 99 (1987).

S.H. Goh, *Thermochimica Acta*, 153, 423 (1989).

N.D. Sachinvala, W.P. Niemczura, and M.H. Litt, *Carbohydr. Res.*, 218, 237 (1991).

Still et al., *Rapid Chromatographic Technique for Preparative Separations with Moderate Resolution*, J. Org. Chem., vol. 43, No. 14, 1978, pp. 2923–2925.

S. Steenken, H.P. Schuchmann, and C. von Sonntag, *The J. of Physical Chemistry*, 79, 763 (1975).

D.C. Nonebel, J.M. Tedder, and J.C. Walton, *Radicals*, Cambridge University Press, London, 1979, 55–61.

H. Zegota and C. von Sonntag, *Z. Naturforsch.*, 32b, 1060 (1977).

C. von Sonntag, M. Dizdaroglu, and D. Schulte–Frohlinde, *Z. Naturforsch.*, 31b, 857 (1976).

J. March, *Advanced Organic Chemistry*, 4th Edition, J. Wiley & Sons Inc., New York, pp. 1006–1010, 1992.

DKS International, Inc., *DK–Ester Sucrose Fatty Acid Ester*, Bulletin 1984.

Bobalek et al., *Preparation and Properties of Linoleate Esters of Sucrose*, I & EC Product Research and Development, Mar. 1963, vol. 2, No. 1, pp. 9–16.

J.K. Kochi, *Organometallic Mechanism and Catalysis*, Academic Press, NY 1978, pp. 346–349.

Osipow et al., *Methods of Preparation . . . Fatty Acid Esters of Sucrose*, Industrial and Engineering Chemistry, Sept. 1956, vol. 48, No. 9, pp. 1459–1462.

G.R. Ames, *Long Chain Derivatives of Monosaccharides and Oligosaccharides*, Chemical Review, 1960, vol. 60, pp. 541–553.

Brimacombe et al., *Alkylation of Carbohydrates Using Sodium Hydride*, Carbohydrate Res., 2 (1966) pp. 167–169.

Peter Munk, J. Wiley, *Introduction to Macromolecular Science*, NY 1989, pp. 153–154.

G. Odian, 3rd Ed., J. Wiley, *Principles of Polymerization*, NY 1991, pp. 150–152.

Matsumoto et al., *Gelation in the Copolymerization of Methyl Methacrylate with Trimethylopropane Trimethracylate*, European Polymer Journal, vol. 25, 1989, pp. 385–389.

POLYMERS HAVING ENHANCED THERMAL STABILITIES AND METHODS FOR THEIR PREPARATION USING STABILIZATION AGENTS 1,6,6'-TRIMETHACRYLOYL 2,3,3',4,4'-PENTA-O-METHYLSUCROSE 1',2,3,3',4,4',6,6'-OCTA-O-ALLYLSUCROSE 1',2,3,3',4,4',6,6'-OCTO-O-CROTYLSUCROSE

RELATED APPLICATIONS

This application is a continuation, of application Ser. No. 08/605,643, filed Feb. 22, 1996, which is a continuation, of application Ser. No. 08/468,315, filed Jun. 6, 1995; in turn a DIV of 08/199,695, filed Feb. 28, 1994, now U.S. Pat. No. 5,470,931; in turn a CIP of 08/028,545, filed Mar. 8, 1993, now abandoned; in turn a CIP of 07/877,813, filed May 4, 1992, now U.S. Pat. No. 5,248,747; in turn a CIP of 07/697,983, filed May 10, 1991, now U.S. Pat. No. 5,116,961; in turn a CIP of 07/623,548, filed Dec. 7, 1990, and now abandoned.

GRANT REFERENCE

The invention described herein was partially funded by U.S.D.A. (A.R.S.) grant number 58-91H2-0-319

BACKGROUND OF THE INVENTION

1. Field of the Invention

The subject invention relates to polymerizable mixtures suitable for the production of polymers having enhanced thermal stability, methods for producing such polymers, and the resulting polymers. The invention also relates to a novel sucrose derivative useful in the polymerizable mixtures.

2. Description of the Related Art

The need to stabilize polymers to increase their usefulness, for example, for high-temperature applications, has long been known in the art. One unsuccessful method of stabilizing polymers tried was the use of crosslinking agents in the synthesis of polymers. See, Grassie et al., *Proc. Royal. Soc. Lond.*, A199, 14 (1949). Compounds such as glycerol, sorbitol, 3,5-dihydroxy-methylbenzyl alcohol and pentaerythritol find wide applicability as polyfunctional crosslinking agents.

A crosslinking agent which is commonly used is 2-ethyl-2-hydroxymethyl-1,3-propanediol or trimethylolpropanetriol. This crosslinking agent, or trifunctional crosslinking agent as it may more accurately be described, is used in particular to produce crosslinked polyesters.

It has additionally been known to functionalize trimethylolpropanetriol further to produce other trifunctional crosslinking agents. For example, it is known that treatment of 2-ethyl-2-hydroxymethyl-1,3-propanediol with acryloyl or methacryloyl chloride will produce 2-ethyl-2-hydroxymethyl-1,3-propanediol triacrylate and 2-ethyl-2-hydroxymethyl-1,3-propanediol trimethacrylate. The resulting polyfunctional crosslinking agents find particular applicability in crosslinking reactions with acrylates and methacrylates.

In such methods, the trimethylolpropane triacrylate or TMPTA and trimethylolpropane trimethacrylate or TMPTMA are then reacted with acrylate and methacrylate monomers, preferably in the presence of a sufficient amount of free radical initiator to facilitate polymerization. Such methods are often used to produce crosslinked thermoset polymers. The resultant thermoset polymers find applicability, e.g., in making automobile coatings and composites. Additionally, crosslinked thermoset polymers are used in bulk, or monomers may be diluted with other compounds to produce adhesives or composite materials.

Despite their widespread use and commercial importance, trimethylolpropane triacrylate or trimethacrylate, pentaerythritol triacrylate or trimethacrylate, ethyleneglycol bisacrylate or bismethacrylate, and methylene bisacrylamide are exceedingly inefficient at crosslinking because of their proclivity to form rings by intramolecular conjugate addition of radicals. Such low crosslinking efficiencies may result in polymers which are not structurally load bearing. Matsumoto and colleagues have shown that trimethylolpropane trimethacrylate (TMPTMA) undergoes intramolecular loop formation 82% of the time, implying an 18% efficiency of crosslinking (Matsumoto, A. et al, *European Polymer Journal*, 1989, Vol. 25, pp. 385–389). Intramolecular loop formation by conjugate addition of radicals should be expected in all crosslinking agents (acrylates, methacrylates, and acrylamides) wherein two mutually reactive functional groups are spanned by 1 to 4 atom bridges. This is because, in such systems, there is no conformational or electronic bias precluding the formation of medium-sized bislactone or bislactam rings. Neither is the formation of macrocycles containing a crosslinker and several monomers precluded by radical mechanisms, as shown below.

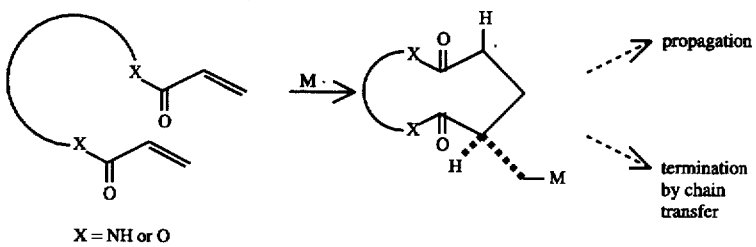

X = NH or O

Furthermore, when acrylic or methacrylic copolymers containing commercial crosslinkers are heated at or beyond their ceiling temperatures (ca. 200° C.), they degrade rapidly. This is because commercial crosslinkers contain no structural elements or mechanisms that quench radicals and stabilize a depolymerizing network.

In order to minimize the recognized problems associated with such crosslinking agents, it had been contemplated in the art to increase the overall concentration of the crosslinking agent in the polymerization mixture as a means of enhancing the degree of crosslinking. However, at high crosslinking agent concentrations, the resultant polymers become brittle and mechanically weak. Additionally, the increased concentration of the crosslinking agent renders the polymers undesirably expensive to produce. For instance, it is described, e.g., in Matsumoto et al, "Gelation in the copolymerization of methyl methacrylate with trimethylolpropane trimethacrylate.", *Eur. Polym. J.*, Vol. 25 (4), pp. 385–389 (1989), that the crosslinking efficiency of trimethylolpropane trimethacrylate is only 18% and that 82% of the crosslinker had internally cyclized despite the fact that an excess of methyl methacrylate was present in the polymerization mixture.

Furthermore, K. Dusek in *Developments in Polymerization-3*, R. N. Howard (editor), Applied Science Publishers, Ltd., London, p. 63, (1982), describes the crosslinking efficiency of methylene bis-acrylamide to be about 10–20% and about 10–20% by weight of methylene bis-acrylamide is needed to effect network formation in hydrogels.

Besides the use of crosslinking agents, other methods of stabilizing polymers have also been utilized. For example, two general stabilizing mechanisms exist for methyl methacrylate polymers by which thermal depropagation may be temporarily arrested. These include (a) blocking depropagation by use of a comonomer such as methyl acrylate, or (b) disrupting depropagation of the PMMA macro radical by use of a radical quencher (see, I. C. McNeill, *Comprehensive Polymer Science*, I. C. McNeill, Ed., Vol. 6, Pergamon Press, New York, pp 451–500, 1989; N. Grassie, *Chemistry of High Polymer Degradation Processes*, Interscience Publishers Inc., New York, 1956; N. Grassie et al, *Chem. Zvesti*, 26, 208 (1972); N. Grassi and G. Scott, *Polymer Degradation & Stabilisation*, Cambridge University Press, London, pp 1–67, 1985; D. H. Solomon, *J. Macromol. Sci.-Chem.*, A17, 337 (1982); N. Grassie, *Pure & Appl. Chem.*, 30, 119 (1972); N. Grassie and H. W. Melville, *Proc. Royal. Soc. Lond.*, A199, 14 (1949); K. A. Holland and I. D. Rae, *Aust. J. Chem.*, 40, 687 (1987); A. Meisters et al, *Poly. Bull.*, 20, 499 (1988); and T. Kashiwagi et al, *Combustion and Flame*, 81, 188 (1990)). Onset of degradation in PMMA copolymers may be delayed up to 300° C. by three methods: (a) copolymerization of MMA with monomers that do not depropagate easily (see, N. Grassie et al, *Eur. Polym. J.*, 17, 589 (1981); N. Grassie et al, *Polym. Degradation Stab.*, 16, 19 (1986); J. Popovic et al, *Polym. Degradation Stab.*, 32, 265 (1991); K. Hayakawa et al, *J. Appl. Polym. Sci.*, 29, 4061 (1984); I. B. Shafranskaya and G. P. Gladyshev, *Izv. Akad. Nauk. Kaz. SSR*, Ser. Khim., 8, 73 (1968); Y. I. Puzin et al, *Vysokomol. soedin.*, Ser. B, 29, 183 (1987); J. San Roman et al, *Rev. Plast. Mod.*, 31, 213 (1976); and V. S. Nikiforenko et al, *Plast. Massy*, 59 (1988)); (b) polymerization of MMA in the presence of chalk fillers (see, K. F. Paus et al, *Plast. Massy*, 13 (1986)), or in porous glass matrices (see, F. M. Aliev and V. N. Zgonik, *Eur. Polym. J.*, 27, 969 (1991)); and (c) polymerization of MMA in the presence of disulfide additives (see U.S. Pat. No. 3,978,022). Thermal stability beyond 300° C. may be provided to PMMA by: (a) anionic polymerization (see, T. Kashiwagi et al, *Macromolecules*, 19, 2160 (1986)); (b) treatment of PMMA with hydrogen in the presence of a catalyst (see, N. Grassie and H. W. Melville, *Proc. R. Soc. London*, A199, 14 (1949); H. H. G. Jellinek, *Degradaton of Vinyl Polymers*, Academic Press, New York, 74, 1965; I. C. McNeil, *Eur. Polym. J.*, 4, 21 (1968); and P. Cacioii et al, *Polym. Bull.* (Berlin), 11, 325 (1984)) or ozone at −78° C. (see, Y. Murashige, Japanese Patent 03045604A2, Feb. 27, 1991, Chem. Abst. 115(2): 9698j), to destroy terminal olefins; (c) copolymerization with 25 to 50 mole percent styrene (see, A. Kaminska et al, *Polym. Networks Blends*, 1, 165 (1991)); and (d) blending PMMA with 25 to 50 weight bisphenol-A polycarbonate (see, A. Rincon, I. C. McNeill, *Polym. Degradation and Stab.*, 18, 99 (1987); and S. H. Goh, *Thermochimica Acta*, 153, 423 (1989)). None of these methods has provided an efficient, simple method for the thermal stabilization of polymers. For example, none of these methods is known to provide long-term thermal stability and many of the methods require a large amount of additive to stabilize PMMA. See, for example, Goh and Rincon et al. Moreover, these methods of stabilization may be quite expensive in practice. Thus, there is an urgent need for thermal stabilizers that will extend the life of the polymer when subjected to heat.

The importance of polymeric stabilizers may be seen in the use of present day petrochemically-derived acrylic and methacrylic crosslinkers in the manufacture of windows, skylights, windshields, insulators, paints, coatings, golf ball cores, and bathroom utility items such as sinks, bathtubs and panels (CORIAN®). The acrylamide crosslinker, for example methylene bisacrylamide, is used in the manufacture of water purification gels, ion-exchange resins, electrophoresis gels, "super slurper" gels, and corrosion inhibitors. The allyl crosslinker is used as a second stage crosslinking agent of vinyl polymers. These vinyl polymers in turn are used for making water-based paints; adhesives for paper, textiles and wood; coating compounds; and thickening agents.

Thus, given the described state of the prior art and the various uses for stabilized polymers, it is clear that improved methods for producing stabilized polymers and improved stabilized polymers resulting from these methods would be highly desirable. In addition to improved methods for producing thermally stable crosslinked polymers, improved non-crosslinked polymers resulting from these methods would be highly desirable.

OBJECTS AND SUMMARY OF THE INVENTION

It is an object of this invention to avoid or alleviate the problems of the prior art.

In its broadest embodiment it is an object of this invention to provide polymers exhibiting improved thermal stability and a method for their production. It is a particular object of the invention to produce polymers having enhanced thermal stability by polymerizing:

(a) an allyl-containing monomer (preferably having 3–20 carbon atoms in its skeleton) which is bonded to at least one primary or secondary hydroxyl group on a saccharide; and (b) one or more monomers selected from the group consisting of methacrylate esters, acrylate esters, acrylamides, styrene and acrylate monomers; wherein the relative amounts thereof and conditions are effective to produce polymers exhibiting enhanced thermal stabilities.

The allyl groups will generally have a unsaturation beta to the ether group.

It is another object of the invention to provide polymers exhibiting enhanced thermal stability and a method for their production by polymerizing a mixture comprising:

(a) a monomer comprising allyl-containing ethers (wherein the allyl-containing group preferably has 3–20 carbon atoms in its skeleton) of a monosaccharide, disaccharide, oligosaccharide, polysaccharide or heteropolysaccharide; and (b) one or more monomers selected from the group consisting of methacrylate ester monomers, acrylate ester monomers, acrylamide monomers and styrene monomers; wherein the relative amounts thereof and conditions are effective to produce polymers exhibiting enhanced thermal stabilities.

It is another object of this invention to provide stable polymers and a method for their production by polymerizing a mixture comprising:

(a) a benzylether compound or benzylether compound comprising long chain hydrocarbon substituents at one or more of positions 2 to 6 of the aromatic ring, wherein preferably the hydrocarbon comprises about 3 to 20 carbon atoms; and (b) one or more monomers selected from methacrylate esters, acrylamides, styrene monomers and acrylate esters; wherein the relative amounts thereof and polymerization conditions are effective to produce polymers exhibiting enhanced thermal stabilities.

It is yet another object of the invention to provide polymers exhibiting enhanced thermal stabilities and a method for their production by polymerizing a mixture comprising:

(a) a long chain allyl-containing ether monomer, preferably having about 3 to 20 carbon atoms and containing more than one double bond in its skeleton; and (b) one or more monomers selected, e.g., from methacrylate esters, acrylate esters, acrylamides and styrene monomers; wherein the relative amounts thereof and polymerization conditions are effective to produce polymers exhibiting enhanced thermal stabilities.

More specifically, it is an object of the invention to provide improved methods for producing stabilized polymers using a saccharide monomer, preferably a sucrose monomer having an allyl-containing group on at least one of the hydroxyl groups. The allyl-containing group on the hydroxyl groups of the sucrose monomer is preferably a long chain ($C_3$–$C_{20}$) allyl-containing ether. More preferably, the long chain ($C_3$–$C_{20}$) allyl-containing ether has more than one double bond in the carbon chain.

It is a specific object of the invention to provide improved methods for producing stabilized polymers comprising methacrylate ester, acrylate ester, acrylamide or styrene monomers using a saccharide monomer, e.g., a sucrose-based monomer containing an unsaturation selected from 1',6,6'-trimethacryloyl-2,3,3',4,4'-penta-O-methylsucrose, 1',2,3,3',4,4',6,6'-octa-O-allylsucrose or 1',2,3,3', 4,4',6,6'-octa-O-crotyl sucrose as a stabilization agent.

It is another object of the invention to provide improved polymers using as a stabilization agent a saccharide monomer, in particular a sucrose-based monomer having an allyl-containing group on at least one of the hydroxyl groups, preferably a long chain ($C_3$–$C_{20}$) allyl-containing ether group on the hydroxyl group, and more preferably, the long chain ($C_3$–$C_{20}$) allyl-containing ether having more than one double bond in the carbon chain.

It is still another object of the invention to provide improved stabilized polymers comprising methacrylate ester, acrylate ester, acrylamide or styrene monomers using a saccharide monomer, in particular a sucrose-based monomer having an allyl-containing group selected from 1',2,3, 3',4,4',6,6'-octa-O-allylsucrose and 1',2,3,3',4,4',6,6'-octa-O-crotylsucrose as a stabilization agent.

It is another object of the invention to provide polymerizable mixtures which upon polymerization result in polymers having enhanced thermal stability, which mixtures comprise a sucrose-based monomer as a stabilization agent having an allyl-containing group on at least one of the hydroxyl groups, preferably a long chain ($C_3$–$C_{20}$) allyl-containing ether group on the hydroxyl group, and more preferably, the long chain ($C_3$–$C_{20}$) allyl-containing ether having more than one double bond in the carbon chain, a monomer which reacts therewith, and optionally a free radical initiator in amounts sufficient to facilitate polymerization.

It is a further object of the invention to provide polymerizable mixtures which upon polymerization result in stabilized polymers having enhanced thermal stability, which mixtures comprise a sucrose-based monomer having an allyl-containing group selected from 1',2,3,3',4,4',6,6'-octa-O-allylsucrose and 1',2,3,3',4,4',6,6'-octa-O-crotylsucrose as a stabilization agent, a methacrylate ester, acrylate ester, acrylamide or styrene monomer and optionally a free radical initiator in relative amounts sufficient to facilitate polymerization and the production of polymers having enhanced thermal stability.

It is still another object of the invention to provide polymers having enhanced thermal stability by polymerizing an acrylic ester of a saccharide and one or more monomers selected from the group consisting of methacrylate esters, acrylate esters, acrylamides and styrene monomers; wherein the relative amounts thereof and conditions are effective to produce polymers exhibiting enhanced thermal stabilities.

It is a specific object of the invention to provide improved methods for producing stabilized polymers comprising methacrylate ester, acrylate ester, acrylamide or styrene monomers using a saccharide monomer, e.g., a sucrose-based monomer containing an acrylic ester, such as 1',6,6'-trimethacryloyl-2,3,3',4,4'-penta-O-methylsucrose.

It is still another object of the invention to provide improved methods for producing non-crosslinked polymers using a non-crosslinking sucrose-based compound or monomer.

It is still a further object of the invention to provide improved methods for producing non-crosslinked polymers comprising methacrylate ester, acrylate ester, acrylamide or styrene monomers using a non-crosslinking sucrose-based additive selected from octa-O-crotyl sucrose, octa-O-methylsucrose, other octa-O-alkylsucroses or partially substituted O-alkyl and O-crotyl sucrose derivatives.

It is another object of the invention to provide improved uncrosslinked thermoplastic polymers using non-crosslinking sucrose-based monomers or additives.

It is a further object of the invention to provide improved uncrosslinked thermoplastic polymers comprising methacrylate ester, acrylate ester, acrylamide or styrene monomers using a non-crosslinking sucrose-based monomer selected from octa-O-crotylsucrose, octa-O-methylsucrose, other octa-O-alkylsucroses, or partially substituted O-methyl, O-crotyl or O-alkyl sucrose derivatives.

It is still another object of the invention to provide polymerizable mixtures which upon polymerization result in non-crosslinked polymers having enhanced thermal stability, which mixtures comprise a non-crosslinking sucrose-based monomer or compound, a monomer which reacts therewith, and optionally a free radical initiator in amounts sufficient to facilitate polymerization.

It is still a further object of the invention to provide polymerizable mixtures which upon polymerization result in non-crosslinked polymers having enhanced thermal stability, which mixtures comprise a non-crosslinking sucrose-based monomer or compound selected from octa-O-crotylsucrose, octa-O-methylsucrose, other octa-O-alkylsucroses, or partially substituted O-methyl, O-crotyl, or O-alkyl sucrose derivatives, a monomer which reacts therewith selected from methacrylate ester, acrylate ester, acrylamide or styrene monomers, and optionally a free radical initiator in amounts sufficient to facilitate polymerization.

It is still further an object of the invention to provide a novel sucrose derivative, 1',2,3,3',4,4',6,6'-octa-O-crotylsucrose, and a method of making it. This novel sucrose derivative is useful in providing polymers exhibiting enhanced thermal stabilities.

It is still further an object of the invention to provide improved methods for producing stabilized polymers comprising methacrylate ester, acrylate ester, acrylamide or styrene monomers using 1',2,3,3',4,4',6,6'-octa-O-crotylsucrose.

It is still further an object of the invention to provide improved stabilized polymers using 1',2,3,3',4,4',6,6'-octa-O-crotylsucrose as a stabilizing agent.

Finally, it is an object of the invention to partially or completely epoxidize the $C_3$–$C_{20}$ allyl-containing groups on octa-O-allylsucrose to generate epoxy-O-allyl derivatives of sucrose and to use these sucrose-based epoxy monomers for the production of epoxy adhesives, paints, moldings, castings and coatings.

The present inventors have surprisingly discovered that not only do the subject sucrose-based stabilizing agents outperform any existing acrylate, methacrylate or acrylamide crosslinker in terms of their efficiency (N. Sachinvala, M. Litt, R. F. Ju, U.S. Pat. No. 5,248,747), but that the sucrose-based stabilization agents provide unprecedented thermal stability to methyl methacrylate and styrene copolymers, among others. The present inventors have confirmed the enhanced thermal stability provided by sucrose-based stabilization agents by: (1) showing the thermal degradation temperatures, glass transition temperatures, and polymer aging studies on poly(methyl methacrylate) copolymers containing crosslinkers 1',6,6'-trimethacryloyl-2,3,3',4,4'-penta-O-methylsucrose and 1',2,3,3',4,4',6,6'-octa-O-allylsucrose, additive 1',2,3,3',4,4',6,6'-octa-O-methylsucrose, and non-crosslinking stabilizer 1',2,3,3',4,4,6,6'-octa-O-crotylsucrose; (2) comparing sucrose-based copolymers directly with methyl methacrylate polymers containing the crosslinker trimethylopropane trimethacrylate; and (3) comparing sucrose-based copolymers with commercial samples of polymers prepared by Du Pont (Lucite®), Rohm & Haas (Plexiglas®), K.S.H. Inc., and Cyro (Acrylite®).

Given the enhanced thermal stability and physical properties inherent to the polymers of the invention, these polymers should comprise particular applicability in fire retardant compositions, and in the preparation of articles and compositions which may be subjected to elevated temperatures.

It is believed by the present inventors that the high thermal stability obtained using the allyl-containing sucrose based monomers which act as crosslinking agents is at least partially attributable to the increased crosslinking efficiency of polymers obtained using said crosslinking monomer. In at least 1',6,6'-trimethacryloyl-2,3,3',4,4'-penta-O-methylsucrose, it is believed that this enhanced crosslinking efficiency occurs at least in part because of the relatively large atom separation between the reactive sites in the crosslinking monomer. For example, in the 1',6,6'-trimethacryloyl-2,3,3',4,4'-penta-O-methylsucrose molecule, the distance between the reactive sites of the 6 and 6' methacryloyl moieties is 16 atoms, the distance between the reactive ends at the 1' and 6' positions is 12 atoms and in addition these two positions are anti in orientation with respect to each other on the fructopyranosyl moiety, the distance between the reactive ends at the 1' and 6 positions is 14 atoms and there is an intervening 2,3,4'-tri-O-methylgluco-pyranosyl moiety. However, the present inventors do not restrict themselves to their belief as to the mechanism by which this or other enhanced thermally stable polymers are obtained in the present invention.

As to both those sucrose-based monomers of the present invention which do not function as crosslinking agents as well as those which do function as crosslinking agents, it is also believed that thermal stability is afforded to polymers containing the sucrose-based alkyl, allyl and crotyl ethers of the present invention due to the ability of these ethers to chain transfer with radicals at elevated temperatures. The normal result of chain transfer at sucrose is fragmentation to generate alkyl, allyl or crotyl radicals (see, S. Steenken et al, *The J. of Physical Chemistry*, 79, 763 (1975); D. C. Nonebel et al, *Radicals*, Cambridge University Press, London, 1979; H. Zegota and C. von Sonntag, *Z. Naturforsch.*, 32b, 1060 (1977); C. von Sonntag et al, *Z. Naturforsch.*, 31b, 857 (1976)) (See FIG. 3). Chain transfer to additive during polymerization will increase the final thermal stability of the polymer, because most polymer chains are terminated with hydrogen (FIG. 1). However, it is believed that there will always be some weak links formed during radical termination. Molecules with such weak links will start depropagating at relatively low temperatures. Chain transferred polymers are more stable than pure polymers. The stability is enhanced by further chain transfer of the depropagating radical on the sucrose moiety. The resulting small radical fragment can then terminate a second depropagating chain. With the allyl-containing compounds of the present invention, copolymerization of allyl and crotyl groups provides additional stability since depropagation will stop when an allyl or crotyl moiety in the chain is reached. This radical will either terminate or chain transfer.

Although not wishing to be bound by any theory, the mechanism of stability that is believed to be operating is as follows: saccharide ethers having many tertiary hydrogens alpha to oxygen are stable to chain transfer at normal polymerization temperatures. At temperatures where the polymer is unstable, these hydrogens chain transfer with radicals and fragment to produce small alkyl, allyl or crotyl radicals which can combine with and terminate the depropagating chain. Thus, the sucrose ether derivatives quench depropagation reactions.

Therefore, the use of sucrose-based monomers having an allyl-containing group on at least one of the hydroxyl groups, preferably a long chain ($C_3$–$C_{20}$) allyl-containing ether group on the hydroxyl group, and more preferably, the long chain ($C_3$–$C_{20}$) allyl-containing ether having more than one double bond in the carbon chain, should result in improved methods of stabilizing monomers, in particular methacrylate ester, acrylate esters, acrylamide and styrene monomers, and should also result in crosslinked or non-crosslinked polymers having enhanced thermal stability and enhanced mechanical properties.

In another aspect of the present invention, the use of 1',6,6'-trimethacryloyl-2,3,3',4,4'-penta-O-methylsucrose results in improved methods of stabilizing monomers.

In another aspect of the present invention, the present inventors have also discovered that the addition of non-crosslinking sucrose based materials, for example the additive 1',2,3,3',4,4',6,6'-octa-O-methylsucrose, under low temperature polymerization conditions, provides more thermal stability to a methyl methacrylate polymer than the crosslinker trimethylolpropane trimethacrylate and parallels the thermal stability of extruded high molecular weight methyl methacrylate polymers.

Therefore, the use of non-crosslinking sucrose-based additives should result in improved methods of producing a non-crosslinked polymer, in particular a non-crosslinked polymer comprised of methacrylate esters, acrylate esters, acrylamides or styrene monomers, and should result in non-crosslinked polymers having enhanced thermal stability.

In another embodiment, the stabilization agent is an acrylic ester derivative of sucrose. Preferably the acrylic ester is 1',6,6'-trimethacryloyl-2,3,3',4,4'-penta-O-methylsucrose. 1',6,6'-trimethacryloyl-2,3,3',4,4'-penta-O-methylsucrose comprises the following structure:

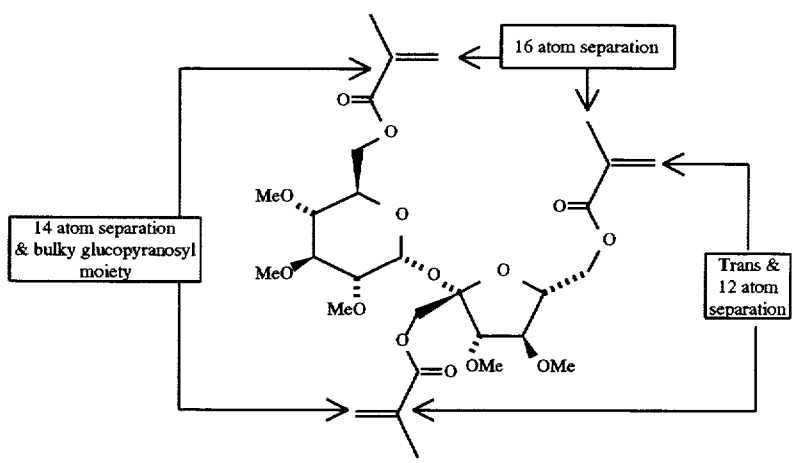

DETAILED DESCRIPTION OF THE PREFERRED EMBODIMENTS

Figure 1:
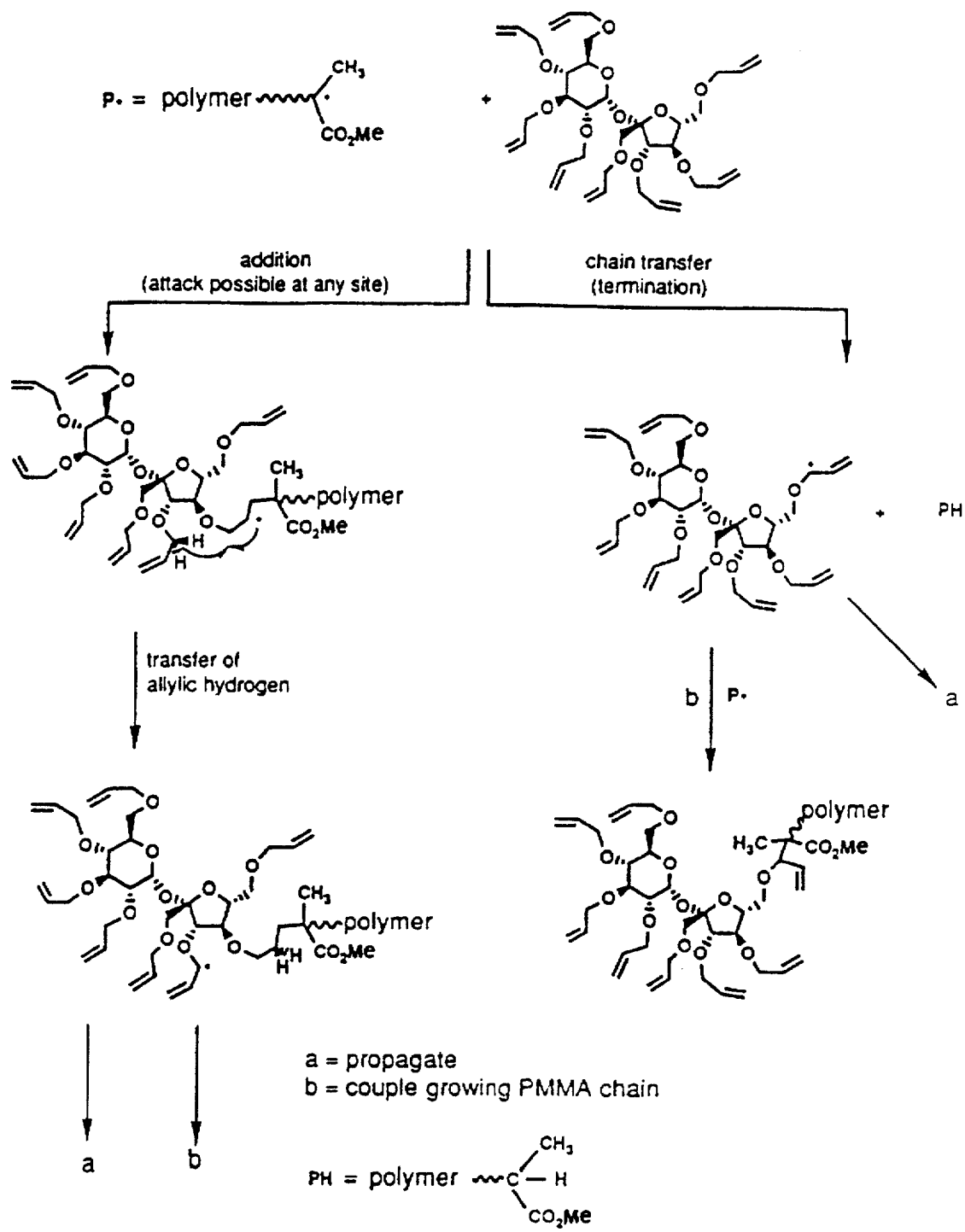
FIG. 1 illustrates the proposed process of stabilization by octa-O-allylsucrose.

As discussed above, the subject invention in one of its preferred embodiments relates to methods of using sucrose-based monomers having an allyl-containing group on at least one of the hydroxyl groups, preferably a long chain (C$_3$–C$_{20}$) allyl-containing ether group on the hydroxyl group, and more preferably, the long chain (C$_3$–C$_{20}$) allyl-containing ether having more than one double bond in the carbon chain, as a novel stabilization agent in polymerization processes, and polymers obtained using this stabilization agent having enhanced thermal stability. The stabilization agent is a sucrose-based monomer having an allyl-containing group on at least one of the hydroxyl groups, preferably a long chain (C$_3$–C$_{20}$) allyl-containing ether group on the hydroxyl group, and more preferably a long chain (C$_3$–C$_{20}$) allyl-containing ether having more than one double bond in the carbon chain. Preferred stabilization agents include 1',2,3,3',4,4',6,6'-octa-O-allylsucrose and 1',2,3,3',4,4',6,6'-octa-O-crotylsucrose.

As can be seen from the structure, inherent in the design of 1',6,6'-trimethacryloyl-2,3,3',4,4'-penta-O-methylsucrose are two structural features that are believed to account for its increased crosslinking efficiency (cf. U.S. Pat. No. 5,248,747) and for the thermal stability this crosslinker affords its copolymers.

First, as explained previously in U.S. Pat. No. 5,248,747 the enhanced crosslinking efficiency of 1',6,6'-trimethacryloyl-2,3,3',4,4'-penta-O-methylsucrose may be attributed to the fact that it is only remotely possible for any two reactive ends of the methacryloyl groups in this crosslinker to coalesce intramolecularly in the presence of excess of the monomer to be polymerized. As can be seen in the above structure, a 16-atom separation exists between the reactive ends of the methacryloyl moieties at the 6 and 6' positions; a 12-atom distance exists between the 1' and 6' methacryloyl moieties, and these groups are anti to each other; and a 14-atom distance exists between the methacryloyl groups at the 1' and 6 ends, and they contain the bulky 2,3,4-tri-O-methylglucopyranosyl group between them.

In these materials, a cleaved chain may still be bound somewhere and may not be free to escape the matrix of the copolymer. Subsequent reunion of the cleaved chains may give rise to additional networks. This may not be the case in thermoset copolymers that contain TMPTMA as the crosslinking agent. Since the crosslinking efficiency of TMPTMA is very low, chains may be completely severed and free to fly away. Equilibrium swelling studies on crosslinked polymers show that this sucrose-based methacrylate crosslinker is 30 to 40% more efficient than commercial trimethacrylate crosslinkers.

Additionally, the methyl groups in 1',6,6'-trimethacryloyl-2,3,3',4,4'-penta-O-methylsucrose are unaffected by heat (provided no acids or nucleophiles are present in the depolymerizing milieu) which contributes to the increased thermal stability of copolymers containing 1',6,6'-trimethacryloyl-2,3,3',4,4'-penta-O-methylsucrose as the stabilizing agent. Moreover, radical cleavage of the disaccharides and hydrogen abstraction for carbons bearing ether groups are believed to yield fragments by chain transfer processes which may rejoin to create further crosslinks.

1',2,3,3',4,4',6,6'-octa-O-allylsucrose is a more economical sucrose derivative which may also be used as a stabilizing agent in order to enhance the thermal properties of the resulting polymer. Its structure is as follows:

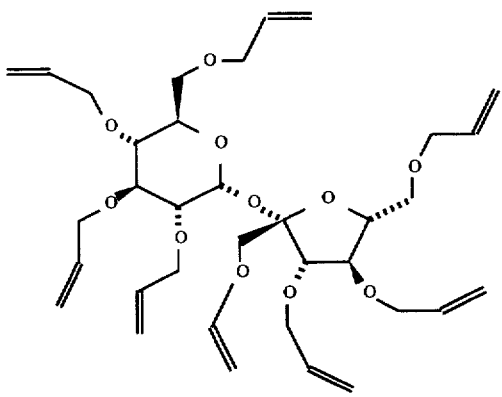

As this allylsucrose derivative has eight double bonds, enough double bonds are available to crosslink several growing polymer chains, resulting in increased crosslinking efficiency. With eight reactive double bonds, octa-O-allylsucrose can crosslink up to eight polymer chains at 100% (theoretical) efficiency. By contrast the commercially available acrylates and methacrylates of, for example, ethyleneglycol, trimethylolpropanetriol and pentaerythritol, can bind only 2 to 4 polymer chains at theoretical efficiency. In this allylsucrose derivative, the allylic double bond is not activated by a neighboring group which could contribute to the stability of the radical generated by the addition of a growing polymer chain radical to the allylic double bond. However, when the polymer chain radical adds across an allylic double bond in octa-O-allylsucrose, the neighboring allylic ethers stabilize the addition by chain transfer of an allylic hydrogen, or the radicals may add monomer and propagate (see FIG. 1.). The resulting allyl radical is then available to engage in intramolecular coupling, crosslinking of another growing methyl methacrylate chain, or initiation of a chain (Peter Munk, Introduction to Macromolecular Science, J. Wiley, New York, 1989, pp. 153–154). It has been found that these mechanisms can take place even when the allylsucrose derivative is only partially substituted. This process of stabilization can be seen in FIG. 1.

Enhanced thermal stability also results since during thermal depolymerization at ca. 200° C., radicals formed by polymer chain cleavage can be quenched by hydrogen transfer from unreacted allylic groups on octa-O-allylsucrose. The resulting allyl radicals would then be available to add to other polymer chain radicals to create additional networks.

1',2,3,3',4,4',6,6'-octa-O-crotylsucrose is a novel effective allyl sucrose derivative stabilization agent which is not a crosslinker. It has been discovered that octa-O-crotylsucrose is a novel effective β-substituted allyl-containing sucrose stabilizing agent. It is not a crosslinking agent like octa-O-allylsucrose. However, it may chain transfer and then the resulting radical may propagate, or generate chain branches by coupling of radicals. (FIG. 1). This compound and its surprising properties were heretofore unknown. Its structure is as follows:

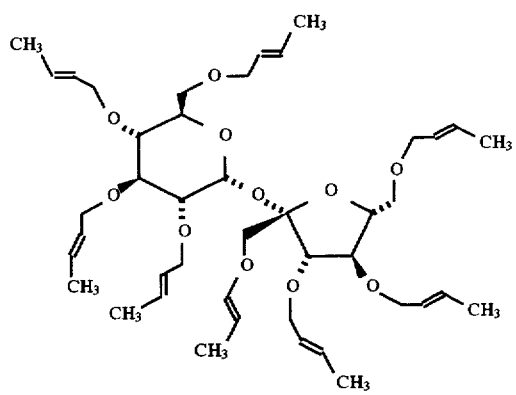

In particular, PMMA's prepared in the presence of octa-O-crotylsucrose are believed to be non-crosslinked, or they may be branched. They are entirely soluble in chloroform. The reduced reactivity of the crotyl group during polymerization with PMMA is believed to be explained by the presence of the terminal electron donating methyl group in the crotyl ether. This methyl group stabilizes the double bond, and sterically diminishes the prospects for the electrophilic methacryl radical to add to it (see, B. Giese and G. Kretzschmer, Chem. Ber., 116, 3267 (1983)). This rationale is supported by the frontier molecular orbital theory (see, B. Giese, Angew. Chem. Intl. Ed. English, 22, 771 (1983)). Since the methacrylate radical is electrophilic, and the crotyl double bond is electron rich, the highest occupied molecular orbital (HOMO) of the crotyl system is suitably placed to interact with the singly occupied molecular orbital (SOMO) of the electrophilic methacryl radical. Simply stated, it is believed that nucleophilic radicals add easily to electron deficient olefins, and electrophilic radicals add easily to electron rich olefins. Since it is believed that in this case this is not happening, as suggested by the fact that PMMA's containing the crotylsucrose are soluble in chloroform, steric factors are preventing addition of the methacryl radical to the crotyl double bond. This is not believed to be the case with PMMA polymers containing octa-O-allylsucrose. Because the terminal double bonds in the allylsucrose are readily accessible, the methacryl radicals add to it to generate a thermoset.

The crotyl ether group, however, may engage in chain transfer reactions at two sites, namely via the methylene between the ether oxygen and the double bond, and the terminal methyl group. This, in turn, may permit the sucrose-based crotyl ether to engage in chain branching by virtue of coupling of radicals. Octa-O-crotylsucrose is present in PMMA polymerthas a plasticizer and reduces the Tg to 110° C. Long term thermal stabilities imparted to the thermoplastic by octa-O-crotylsucrose are unprecedented, since PMMA containing one mole % octa-O-crotylsucrose survives thermal aging at 200° C. for 1 and 8.5 days, with only 6 and 22% loss in original mass respectively. Apart from slight yellowing, this polymer does not sag or flow after 24 h at 200° C. in air.

The stabilization agent comprising a sucrose-based monomer having an allyl-containing group on at least one of the hydroxyl groups, preferably a long chain ($C_3$–$C_{20}$) allyl-containing ether group on the hydroxyl group, and more preferably the long chain ($C_3$–$C_{20}$) allyl-containing ether having more than one double bond in the carbon chain, may be synthesized by methods well known to those skilled in the art. Commercially available monomers of the sucrose-based monomers may be used as obtained from the manufacturer.

Generally, all monomers were prepared in dry glassware under an inert atmosphere, using conditions described in Sachinvala, N. D. et al., *Carbohydrate Research*, 1991, Vol. 218, pp. 237–245. Proton nuclear magnetic resonance (NMR) spectra were recorded at 500.11 MHz, and carbon-13 NMR spectra were recorded at 125.76 MHz, using a General Electric GN Omega 500 spectrometer. Fast atom bombardment (FAB) mass spectra were obtained on a VG instrument (Model 70 S.E.) using xenon as a bombarding gas. Molecular ions were verified as |M+1|$^+$, |M+K|$^+$ or |M+Na|$^+$ by addition of potassium or sodium iodide to the sample matrix. All organic reagents and solvents (reagent grade, Aldrich Chemical Company) used in monomer syntheses were purified and dried before use according to procedures outlined by Perrin et al (*Purification of Laboratory Chemicals*, 2nd edition, Pergamon Press, Oxford, 1990). Flash column chromatography was performed according to Still et al (*J. Org. Chem.*, 1973, Vol. 73, pp. 2923–2925). Optical rotations were obtained on a Jasco DIP-370 polarimeter at 598 nm. Elemental analyses were performed by Desert Analytics (Tucson, Ariz.).

In particular, the 1',6,6'-trimethacryloyl-2,3,3',4,4'-penta-O-methylsucrose stabilization agent may be synthesized by the method which is described in applicants' commonly assigned patent, U.S. Pat. No. 5,116,961. The disclosure contained therein relating to the synthesis of 1',6,6'-trimethacryloyl-2,3,3',4,4'-penta-O-methylsucrose is hereby incorporated by reference in its entirety.

For the synthesis of 1',2,3,3',4,4',6,6'-octa-O-allylsucrose, the procedure of Brimacombe, J. S. et al (*Carbohydrate Research*, 1966, Vol. 2, pp. 167–169) was modified, and the solvent DMF (because of its hepatotoxicity and incompatibility with sodium hydride at high temperatures) was replaced with DMSO (dimethylsulfoxide) or DMAC (dimethyl acetamide). A dispersion of sodium hydride (60% in oil, 8.4 g, 210 mmol) was washed with dry hexanes (4×15 mL), suspended in DMSO (300 mL), and then treated at 10° C. with a solution of sucrose (5.0 g, 14.62 mmol) in DMSO (30 mL). The temperature of the reaction mixture was monitored internally and allowed to attain 35°–40° C., and the contents stirred for 90 minutes. The resulting yellow mixture was then cooled to 10° C., treated with allyl bromide (13 mL, 150.22 mmol, added over 30 minutes), then allowed to attain a temperature of 40° C. and stirred overnight. Subsequently, the mixture was quenched with 5% aqueous sodium hydroxide (30 mL) at 15° C., diluted with water 500 mL, and extracted with ethylacetate (4×100 mL). The organic extracts were combined, washed with brine (3×150 mL), dried over anhydrous sodium sulfate, filtered, and concentrated in vacuo. Flash column chromatography of the residue on a silica gel (230–400 mesh) column (7 cm×15 cm) using hexanes (2 L), and 10% ethylacetate in hexanes (3 L) provided the desired octa-O-allylsucrose (9.68 g) in 87% yield.

Octa-O-crotylsucrose was prepared in DMAc as well as DMSO (95% yield) using the same procedure as above, except that crotyl chloride was used instead of allyl bromide. Crotyl chloride (98.8%) is predominantly trans, and contains 14% of the cis isomer, and 1.2% 3-chloro-1-butene. Octa-O-crotylsucrose therefore consists of a mixture of cis and trans isomers. Because of this, NMR assignments of the sucrose portion of this compound are without coupling constants, and for the eight crotyl substituents on sucrose, only the ppm ranges of the olefin, methylene and the methyl groups within the crotyl substituents are given. The following characteristics were determined: $^1$H NMR (500 MHz Acetone-d$_6$) δ: 1.60–1.70 (Crotyl methyl protons), 3.165 (H-2), 3.195 (H-4), 3.376 (H-1'b), 3.515 (H-3), 3.536 (2 protons, H-6a, H-6b), 3.565 (H-1'a), 3.587 (H-6'b), 3.689 (H-6'a), 3.825 (H-5'), 3.85–4.30 (crotyl methylene protons), 3.944 (H-5), 3.969 (H-4'), 4.151 (H-3'), 5.428 (H-1), and 5.50–5.78 (crotyl olefinic protons); $^{13}$C NMR (125.76 MHz Acetone-d$_6$) δ17.8–18.0 (crotyl CH$_3$ groups), 69.714 (C-6), 71.5–74.5 (crotyl CH$_2$ groups), 72.091 (C-1'), 72.091 (C-5), 72.402 (C-6'), 78.115 (C-4), 80.181 (C-5'), 80.255 (C-2), 82.025 (C-3), 82.769 (C-4'), 83.703 (C-3'), 90.386 (C-1), 105.035 (C-2'), and 128.0–130.0 (crotyl olefinic CH groups); E.I. mass for C$_{44}$H$_{70}$O$_{11}$ calc. 775.00; found |M−1|$^+$=774.

Other sucrose-based monomers having an allyl-containing group on at least one of the hydroxyl groups, preferably a long chain (C$_3$–C$_{20}$) allyl-containing ether group on at least one of the hydroxyl groups, and more preferably, the long chain (C$_3$–C$_{20}$) allyl-containing ether having more than one double bond in the carbon chain, may be similarly synthesized by methods well known to those skilled in the art and as generally described above. Depending on the specific structure, these monomers may be crosslinking as with the octa-O-allylsucrose, or not crosslinking, as with the octa-O-crotylsucrose. Thus, both stabilized crosslinked and non-crosslinked polymers may be obtained using these sucrose-based monomers.

These stabilization agents will comprise particular applicability for stabilizing methacrylate esters, acrylate esters, acrylamide and styrene polymers. However, the stabilization agents should also be suitable for stabilizing a variety of polymers which are well known and available in the art.

For example, suitable monomers in the present invention may include methyl methacrylate, methacrylic acid, hydroxyethyl methacrylate, methyl acrylate, acrylic acid, styrene, acrylonitrile, and the like. However, as noted, it is preferred that the monomers used are methacrylate or acrylate esters, such as methyl methacrylate, and acrylamide monomers. Such monomers may be synthesized by methods well known in the art, or may be obtained commercially.

The amount of stabilization agent utilized will comprise those amounts which will result in a polymer having the desired degree of stabilization. Typically, the amount of the stabilization agent utilized will range from about 0.01 to about 50 mole percent, and more preferably, from about 0.1 to about 10 mole percent. However, the particular amount utilized may be varied depending upon the particular monomer or monomers to be polymerized and the desired properties of the resultant polymers.

As previously stated, the subject invention also relates to methods of using non-crosslinking sucrose-based monomers or additives in polymerization processes, and non-crosslinked polymers having enhanced thermal stability obtained using these non-crosslinking sucrose-based additives. The non-crosslinking sucrose-based additive will preferably comprise an alkyl or crotyl-containing ether on at least one of the hydroxyl groups of sucrose. Preferred non-crosslinking sucrose-based additives include octa-O-methylsucrose, and other octa-O-alkylsucroses or partially substituted O-alkylsucroses. Octa-O-methylsucrose, for example, comprises the following structure:

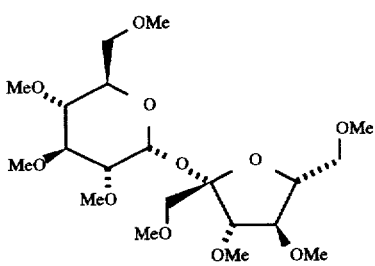

The octa-O-methylsucrose, for example, may be prepared in DMSO or DMAc using the same procedure as described above for octa-O-allylsucrose, except that methyl chloride, methyl bromide, methyl iodide, or dimethysulfate are used instead of allyl bromide. Preferably, the octa-O-methylsucrose is prepared in DMSO with methyl iodide.

Other octa-O-alkylsucrose monomers may be similarly synthesized using the appropriate alkyl chloride, bromide or iodide as well as by other methods well known to those skilled in the art.

Other non-crosslinking sucrose-based additives may be similarly synthesized by methods well known by those skilled in the art. The monomers may also be purchased and used as obtained commercially from the manufacturer. For example, sucrose octaacetate® and sucrose diacetate hexaisobutyrate® may be purchased from Eastman Kodak and used as obtained. However, these additives are not as effective for stabilization of polymers.

Penta-O-methylsucrose triacetate may be prepared as follows. To a solution of penta-O-methylsucrose (1.0 g, 2.43 mmol) in pyridine (100 mL) at 0° C., acetic anhydride (3 mL, 31.8 mmol) is added and the mixture allowed to stir at room temperature for two days. The volatile contents of the reaction mixture are then removed in vacuo and the residue is reconstituted in ethylacetate and washed successively with 1N HCl, saturated aqueous sodium bicarbonate, water, and brine. The organic layer is then dried over sodium sulfate and concentrated to an oily residue in vacuo. The oily material is then purified by flash column chromatography on silica gel using 50% ethylacetate in hexanes to provide the title compound (1.31 g) in 96% yield.

These non-crosslinking sucrose-based monomers or compounds will comprise particular applicability for polymerizing methacrylate esters, acrylate esters, acrylamide and styrene monomers. However, the sucrose-based monomer or compound additives would also be suitable for polymerizing a variety of monomers which are well known and available in the art.

For example, suitable monomers in the present invention may include methyl methacrylate, methacrylic acid, hydroxyethyl methacrylate, methylacrylate, acrylic acid, styrene, acrylonitrile, and the like. However, as noted, it is preferable that the monomers used are methacrylate or acrylate esters, such as methyl methacrylate, and acrylamide monomers.

The amount of sucrose-based monomer or compound utilized will comprise those amounts which will result in a polymer having the desired properties and degree of non-crosslinked polymerization. Typically, the amount of the non-crosslinking additive utilized will range from about 0.01 to about 50 mole percent, and more preferably from about 0.1 to about 10 mole percent. However, the particular amount utilized may be varied depending upon the particular monomer to be polymerized and the desired properties of the resultant polymers. For example, the non-crosslinking sucrose-based additives or compounds of the present invention may be used as an additive in the polymerization process to result in a polymer having enhanced thermal stability.

The polymerizable mixture of the sucrose-based monomer or compound and the monomer to be polymerized will optionally contain a free radical initiator, which can be a thermal initiator, photo initiator, chemical initiator, or a catalyst to initiate polymerization. However, an initiator or catalyst is not required since polymerization can also be induced by thermal means or by radiation.

The particular initiator or catalyst selected will depend upon the conditions at which the polymerization is to be effected and the desired properties of the resultant polymers. Suitable initiators and catalysts for polymerization processes are well known to those skilled in the art. Such initiators include, for example, alkoxy alkyl benzophenones, acyl peroxides and azobutyronitriles. This list is intended to be exemplary only and other known initiators are within the scope of the present invention.

The actual amount of the initiator or catalyst utilized will typically range from about 0.01 to about 5% by weight, and preferably from about 0.1 to about 3% by weight. However, these amounts will vary dependent upon the particular initiator or catalyst selected, and the conditions of polymerization.

Methods for producing stabilized polymers by the reaction of a monomer and a stabilization and/or crosslinking monomer are well known to those skilled in the art. In the present invention, the particular polymerization conditions will vary dependent upon factors including, e.g., the particular agent used, the particular monomer which is reacted with the agent, the relative proportions thereof, the degree of crosslinking desired (if applicable), the desired molecular weight of the polymer, whether polymerization is effected in bulk or in solution, the particular solvent, the presence of a free radical initiator, and the amount thereof, among other factors. The determination of suitable conditions for polymerization is within the level of skill in the art.

Methods for producing non-crosslinked polymers by the reaction of a monomer and a non-crosslinking sucrose-based monomer or compound are well known to those skilled in the art. In the present invention the particular polymerization conditions will vary dependent upon factors including, e.g., the particular non-crosslinking additive used, the particular monomer which is reacted with the non-crosslinking additive, the relative proportions thereof, the desired molecular weight of the polymer, whether polymerization is effected in bulk or in solution, the particular solvent, the presence of a free radical initiator, and the amount thereof, among other factors. The determination of suitable conditions for polymerization is within the level of skill in the art.

In order to further illustrate the present invention and the advantages thereof, the following specific examples are given, it being understood that the same is intended only as illustrative and in nowise limitative.

EXAMPLES

In order to establish the enhanced thermal stability of the stabilized polymers produced using the sucrose-based monomer containing an allyl-containing group as a stabilizing agent, the present inventors compared the thermal properties, i.e., glass transition temperature and thermal degradation temperature, of polymers produced using the sucrose-based stabilizing agents of the subject invention to the thermal properties of crosslinked polymers produced using conventional crosslinking agents, e.g., trimethyl propane trimethacrylate. The thermal stability of non-crosslinked polymers produced using non-crosslinking sucrose-based additives of the invention were also compared to crosslinked polymers. The thermal degradation was measured graphically by drawing two intersecting tangents continuing from the slopes on the thermal gravimetric analyses (TGA), and their intersection was defined as the onset of catastrophic degradation for a given polymer sample.

In the examples, the copolymers were prepared in glass tubes 50 cm in length, 0.5 cm inside diameter and 2 mm wall thickness. Trimethylolpropane trimethacrylate (TMPTMA technical grade), chlorobenzene, and methyl methacrylate (MMA), were purchased from Aldrich Chemical Company and used directly. Additives such as sucrose octaacetate® and sucrose diacetate hexaisobutyrate® were purchased from Eastman Kodak and used as obtained from the manufacturer. All copolymers were prepared in bulk, except copolymers containing one mole percent of either TMPTMA or penta-O-methylsucrose trimethacrylate [(MAc)$_3$(OMe)$_5$sucrose].

Example 1

Reagents were mixed to produce crosslinked MMA copolymers containing various mole percentages of TMPTMA, (MAc)$_3$(OMe)$_5$sucrose and octa-O-allylsucrose. The samples were subsequently diluted with an equal volume of chlorobenzene and the mixtures set to polymerize.

Table 1 shows the amounts (in mL) of stock solutions mixed to achieve the indicated mole percentages of crosslinking agents. The stock solutions used to prepare the polymerization mixtures were as follows:

A ten weight percent stock solution was prepared by mixing TMPTMA (2.9284 g) in MMA (26.355 g, 28.2 mL).

A ten weight percent stock solution was prepared by mixing (MAc)$_3$(OMe)$_5$sucrose (2.9284 g) in MMA (26.355 g, 28.2 mL).

A fifty percent stock solution was prepared by mixing octa-O-allylsucrose (4.25 g) in MMA (4.25 g).

Azobisisobutyronitrile (AIBN, 300 mg) was dissolved in chlorobenzene (110 mL) to give a solution concentration of 2.727 mg/mL. The same quantity of AIBN was used to prepare a solution of AIBN in MMA.

TABLE 1

| | Quantities of Monomer, Crosslinker and Solvent Used in Copolymer Preparation | | |
|---|---|---|---|
| Mole % TMPTMA | mL of Stock Solution (10% TMPTMA in MMA) | mL of Stock Solution (AIBN in MMA 2.727 mg/mL) | mL of Chlorobenzene |
| 1.00 | 3.38 | 7.30 | 10.68 |
| 0.75 | 2.54 | 8.14 | 10.68 |
| 0.50 | 1.69 | 8.99 | 10.68 |
| 0.25 | 0.85 | 9.83 | 10.68 |
| 0.10 | 0.34 | 10.34 | 10.68 |
| 0.05 | 0.17 | 10.51 | 10.68 |

TABLE 1-continued

| | Quantities of Monomer, Crosslinker and Solvent Used in Copolymer Preparation | | |
|---|---|---|---|
| Mole % (MAc)$_3$(OMe)$_5$-sucrose | mL of Stock Solution [10% (MAc)$_3$(OMe)$_5$-sucrose in MMA] | mL of Stock Solution (AIBN in MMA 2.727 mg/mL) | mL of Chlorobenzene |
| 1.00 | 6.16 | 4.52 | 10.68 |
| 0.75 | 4.62 | 6.06 | 10.68 |
| 0.50 | 3.08 | 7.60 | 10.68 |
| 0.25 | 1.54 | 9.14 | 10.68 |
| 0.10 | 0.62 | 10.06 | 10.68 |
| 0.05 | 0.31 | 10.37 | 10.68 |
| Mole % Octa-O-allylsucrose | mL of Stock Solution (50% Octa-O-allylsucrose in MMA) | mL of Stock Solution (AIBN in MMA 2.727 mg/mL) | mL of Chlorobenzene |
| 3.00 | 2.28 | 5.19 | 0 |
| 2.50 | 1.90 | 5.40 | 0 |
| 2.00 | 1.50 | 5.61 | 0 |
| 1.50 | 1.12 | 5.80 | 0 |
| 1.00 | 0.75 | 6.00 | 0 |
| 0.50 | 0.37 | 6.22 | 0 |
| 0.10 | 0.075 | 6.37 | 0 |

Example 2

Reagents were mixed to produce linear MMA copolymers containing one mole percentage of non-crosslinking additive. The non-crosslinking additives mixed with the MMA copolymers included: sucrose octaacetate, sucrose diacetate hexaisobutyrate, octa-O-methylsucrose, penta-O-methylsucrose triacetate and octa-O-crotylsucrose. The polymerization mixtures were prepared using a ten weight percent stock solutions of each additive. Table 2 shows the concentration of each non-crosslinking additive mixed to produce MMA copolymers containing one mole percent of each: sucrose octaacetate, sucrose diacetate hexaisobutyrate, octa-O-methylsucrose, penta-O-methylsucrose triacetate and octa-O-crotylsucrose using the ten weight percent stock solutions of each additive. The non-crosslinking additive was then mixed with the appropriate volumes of MMA to get a final one mole percent concentration.

$$10\% \text{ stock solution} = \frac{1 \text{ g sample}}{1 \text{ g sample} + 9 \text{ g } MMA} = \frac{1 \text{ g sample}}{1 \text{g} + 9.36 \text{ mL } MMA}$$

The samples were subsequently diluted with an equal volume of chlorobenzene and the mixtures set to polymerize.

TABLE 2

| | PMMA Containing Non-Crosslinking Additives | | |
|---|---|---|---|
| Mole % Additive | mL of Stock Solution (Additive + MMA) | mL of Stock Solution (AIBN in MMA 2.727 mg/mL) | ml of Chlorobenzene |
| 1 | sucrose octaacetate + MMA stock solution (6.79 mL) | 3.89 | 10.68 |
| 1 | sucrose diacetate hexaisobutyrate stock solution (8.47 mL) | 2.21 | 10.68 |
| 1 | octa-O-methylsucrose + MMA stock solution (4.54 mL) | 6.14 | 10.68 |

TABLE 2-continued

PMMA Containing Non-Crosslinking Additives

| Mole % Additive | mL of Stock Solution (Additive + MMA) | mL of Stock Solution (AIBN in MMA 2.727 mg/mL) | ml of Chlorobenzene |
|---|---|---|---|
| 1 | penta-O-methylsucrose triacetate + MMA stock solution (5.39 mL) | 5.29 | 10.68 |
| 1 | octa-O-crotylsucrose + MMA stock solution (7.74 mL) | 2.94 | 10.68 |

Example 3

The polymer tubes to be used for the polymerization mixtures were silanized by rinsing each tube with a solution of trimethylsilylchloride in methylene chloride (1:1) and subsequently cleaned with methylene chloride (2×), acetone (2×), and deionized water (1×). The tubes were then dried overnight at about 100° C. The polymerization mixtures of Examples 1 and 2, containing monomers, crosslinkers, additives and solvents in amounts as indicated in Tables 1 and 2, were mixed as needed in a one neck flask at room temperature, and purged for 2 to 3 minutes with helium gas. The mixture was then transferred via a teflon coated syringe containing a teflon needle to two polymerization tubes and filled to the 30 cm mark. The contents of the polymerization tubes were degassed by the freeze thaw method in vacuo (4 cycles), sealed with a propane gas torch and allowed to polymerize in a water bath at about the following temperatures and time regimens: 25° C., 2 days; 35° C., 2 days; 45° C., 1 day; 55° C., 1 day; 65° C., 1 day; 70° C., 1 day. The polymer samples were then removed from the tubes, cut into 1 cm cylinders and stored in airtight amber bottles.

Example 4

Thermal Analyses

Thermogravimetric analyses (TGA) on all polymers, regardless of their mode of polymerization, were conducted after heating samples in an oven set at about 140° C. for 12 hours. Measurements were made on a Shimadzu TGA-50 under nitrogen (flow rate 20 mL/min) with heating of the polymer from about room temperature to about 450° C. (rate of heating 10°/min). Differential scanning calorimetry (DSC) on all dry polymer samples was made using a Shimadzu DSC-50 under nitrogen (flow rate 20 mL/min) with heating of the polymer from about room temperature to about 200° C. (rate of heating 20°/min). After reaching about 200° C., the polymer was allowed to cool convectionally (no additional means of rapid cooling was applied), and reheated to about 200° C. under the exact conditions used in the first run. Data was collected during and after the second scan.

The glass transition and thermal degradation temperatures of non-crosslinked MMA polymers, crosslinked MMA copolymers containing crosslinkers TMPTMA, (MAc)$_3$(OMe)$_5$sucrose or octa-O-allylsucrose, and MMA copolymers containing non-crosslinking sucrose-based additives were compared. The results are shown in Table 3.

The results indicate that an unprecedented amount of thermal stability was afforded to the network copolymers containing sucrose-based crosslinkers, whereas no thermal stability was afforded to MMA copolymers containing TMPTMA.

As shown in Table 3, the non-crosslinked PMMA polymers and copolymers are: our laboratory bulk polymer sample, Lucite-L® (DuPont), Plexiglass® UF-3 Rohm and Haas), which may contain the thermal stabilizer di-tert-dodecyl disulfide), SAFE-T-VUE U-012A (KSH, Inc.) Acrylite® and Plexiglass® polymers (Cyro), and various PMMA copolymers containing sucrose-based additives octa-O-methylsucrose, penta-O-methylsucrose triacetate, sucrose octaacetate and sucrose diacetate hexaisobutyrate (Eastman Kodak).

Figure 2:
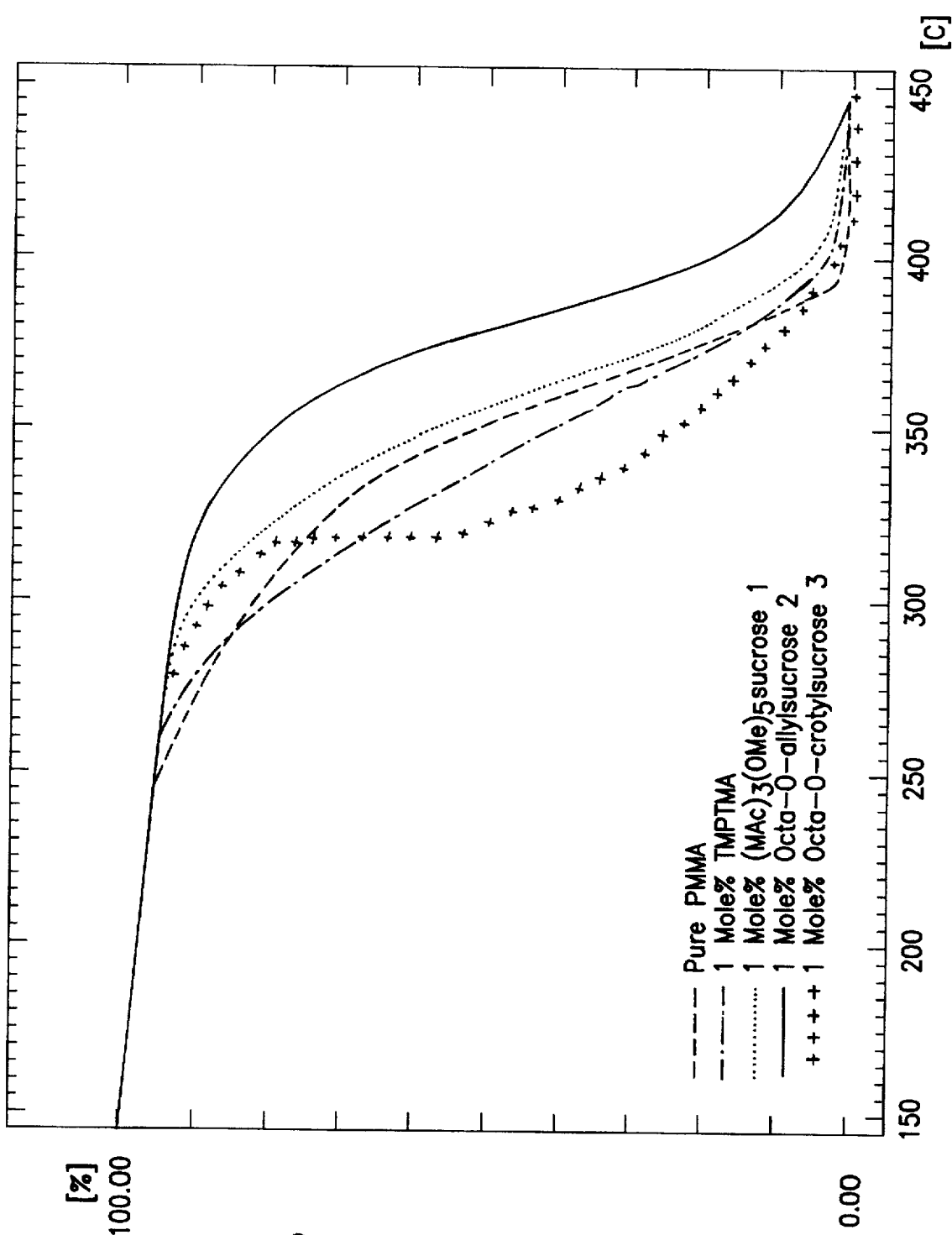
FIG. 2 represents the thermal degradation profiles of PMMA and PMMA copolymers containing one mole percent TMPTMA, (MAc)$_3$(OMe)$_5$sucrose, octa-O-allylsucrose or octa-O-crotylsucrose.
Figure 3:
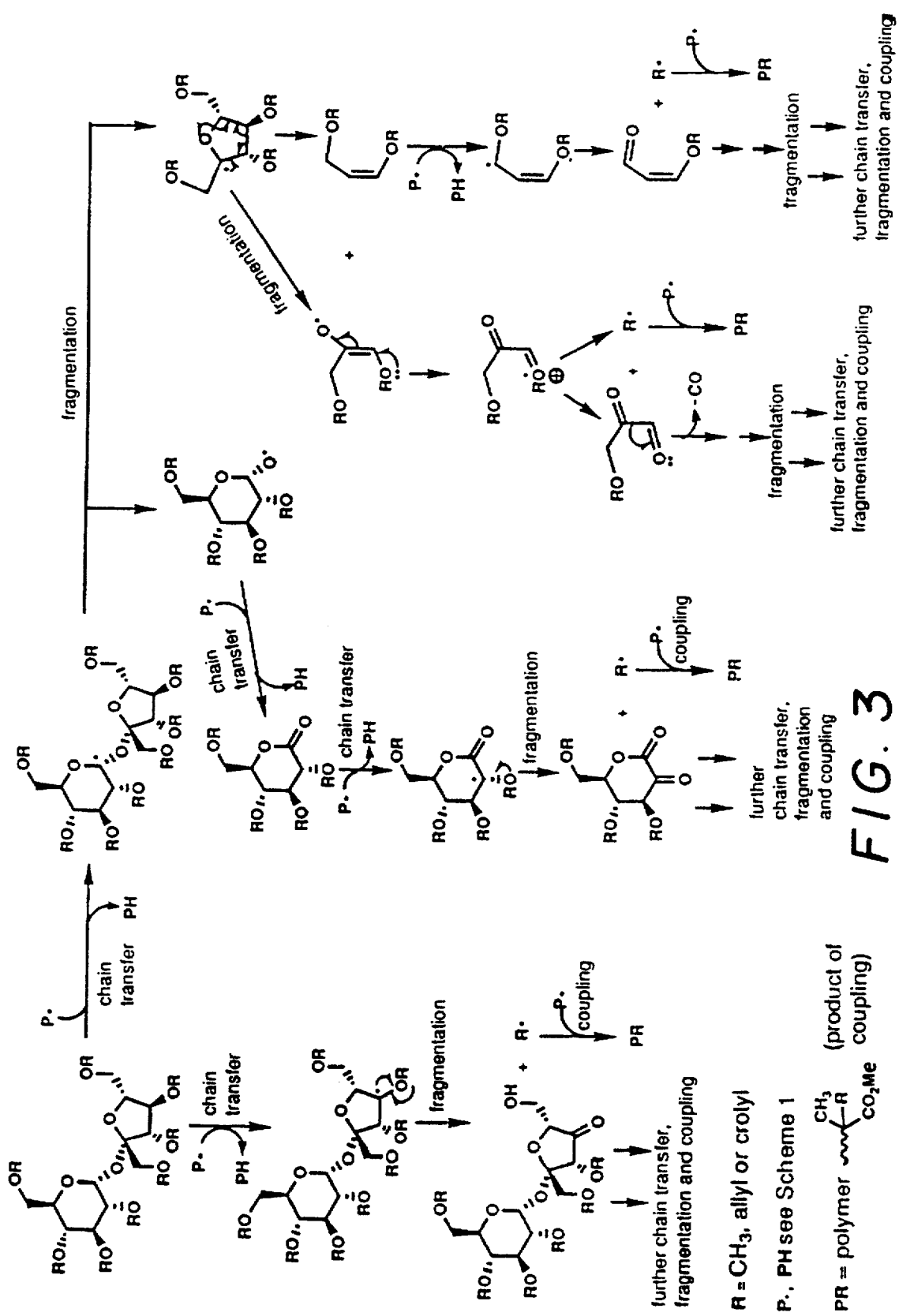
FIG. 3 shows the proposed mechanism for thermal stabilization of PMMA by octasubstituted alkyl, allyl and crotyl ether sucrose derivatives.

The thermal degradation profiles of PMMA and copolymers containing one mole percent TMPTMA, (MAc)$_3$(OMe)$_5$sucrose, octa-O-allylsucrose or octa-O-crotylsucrose were also produced and are shown in FIG. 2.

The thermal degradation studies on these non-crosslinked polymers and copolymers showed that octa-O-methylsucrose provides more thermal stability to PMMA than the crosslinker TMPTMA, or the Rohm & Haas product Plexiglass® UF-3 which may contain the di-tert-dodecyl disulfide thermal stabilizer (Carson, W. F., Jr., U.S. Pat. No. (3,586,292, issued Jul. 8, 1974). Furthermore, a comparison of the sucrose-based additives reveals that low molecular weight ester appendages to the secondary hydroxyl groups on sucrose are thermally destabilizing, whereas methyl, alkyl, allyl or crotyl ethers on the hydroxyl groups of sucrose are thermally stabilizing.

For example, the thermal degradation of PMMA crosslinked with octa-O-allylsucrose shows the enhanced properties achieved using the octa-O-allylsucrose as a crosslinker. PMMA copolymers containing one mole percent octa-O-allylsucrose are exceptionally heat stable. They degrade at 354° C. by thermogravimetric processes, and they lose only about thirty percent of their original weight upon heating at 200° C. for 17 days. There is no PMMA copolymer known to date that is capable of withstanding these thermal-aging conditions for this length of time.

The glass transition temperatures of copolymers containing octa-O-allylsucrose are lowered as the concentration of octa-O-allylsucrose increases in the copolymers from zero mole percent (Tg=116° C.) to 3 mole percent (Tg=94° C.). These glass transition temperatures can be further lowered and more flexibility can possibly be imparted to the PMMA copolymers if the length of chain of the allyl group is increased.

With respect to the PMMA copolymers containing one mole percent each of sucrose octaacetate, sucrose diacetate hexaisobutyrate, penta-O-methylsucrose triacetate, and octa-O-methylsucrose, the thermogravimetric degradation processes show that the PMMA copolymers containing penta-O-methylsucrose triacetate, sucrose octaacetate, and sucrose diacetate hexaisobutyrate (at 283° C., 278° C., and 247° C., respectively) degrade at or below the degradation temperature for pure PMMA (ca. 284° C.). Hence, use of these esters to inexpensively create mixed methacrylate-isobutyrate or methacrylate-acetate derivatives would be ill-advised. Molecular models show that the acetate groups of these additives are syn to the hydrogens on the adjacent carbons of the sugar. As shown below, these hydrogens would therefore be readily available for thermal syn-elimination via favorable six-membered transition states.

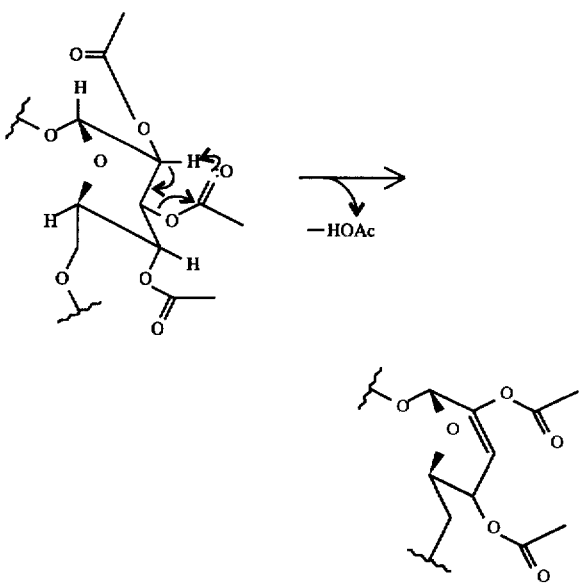

Such pyrolytic degradations of acetyl, propionyl, isobutyryl, and benzoyl groups are well documented (March, J., *Advanced Organic Chemistry*, 4th Ed., J. Wiley, New York, 1992, pp. 1006–1010; Kochi, J. K., *Organic Mechanisms and Catalysis*, Academic Press, New York, 1978, pp. 346–349). It is also shown in the literature that esters of long chain ($C_{12}$–$C_{18}$) carboxylic acids of monosaccharides and long chain ($C_{10}$–$C_{18}$) sucrose polyesters are stable against thermal degradation up to about 200° C. (Bobalek et al., *I&EC Product Research and Development*, 1963, Vol. 2, pp. 9–16; Anderson, A. W. et al., U.S. Pat. No. 2,908,681, issued Oct. 13, 1959; Martin, J. B., U.S. Pat. No. 2,997,492, issued Aug. 22, 1961; Sucrose Fatty-Acid Esters "D-K ESTER", DKS International, Inc., Bulletin 1984; Ames, G. R., *Chemical Reviews*, 1960, Vol. 60, 541–553; Osipow, L. et al., *Industrial and Engineering Chemistry*, 1956, Vol. 48, 1459–1462; Haas, H., Snell, F. D., U.S. Pat. No. 2,893,990, issued Jul. 7, 1959).

However, when the PMMA was prepared with octa-O-methylsucrose (maximum temperature during preparation=70° C.) and its thermal degradation studied, the present inventors found this PMMA to be degrading at temperatures 25° higher than PMMA copolymers containing TMPTMA, 17° higher than die-cast Plexiglass®, and at about the same temperature as high molecular weight extruded PMMA polymers (which are prepared at high temperatures).

PMMA containing octa-O-crotylsucrose is more thermally stable than MMA reacted with TMPTMA and most commercial polymers.

TABLE 3

Glass Transition Temperature and Thermal Degradation Temperatures of PMMA and Copolymers Containing Various Mole Percentages of TMPTMA and Sucrose-Based Additives

| Mole % Crosslinker | Glass Transitions Temperature (°C.) | Thermal Degradation Temperature (°C.) |
|---|---|---|
| Pure PMMA (no crosslinker, laboratory prep) | 116 | 284 |
| Lucite-L ®, Du Pont | 114 | 284 |
| Plexiglas ® UF-3, Rohm & Haas | 123 | 292 |
| Acrylite ® FF, Cyro | 114 | 282 |
| Acrylite ® GP, Cyro | 114 | 320 |
| SAFE-T-VUE ® U-012a, K.S.H. Inc. | 116 | 312 |
| PMMA copolymer containing TMPTMA | | |
| 1.00 mole % TMPTMA | 108 | 283 |
| 0.75 mole % TMPTMA | 108 | 275 |
| 0.50 mole % TMPTMA | 109 | 286 |
| 0.25 mole % TMPTMA | 109 | 284 |
| 0.10 mole % TMPTMA | 109 | 280 |
| 0.05 mole % TMPTMA | 110 | 287 |
| PMMA copolymer containing (MAc)$_3$(OMe)$_5$sucrose | | |
| 1.00 mole % (MAc)$_3$(OMe)$_5$sucrose | 106 | 320 |
| 0.75 mole % (MAc)$_3$(OMe)$_5$sucrose | 106 | 316 |
| 0.50 mole % (MAc)$_3$(OMe)$_5$sucrose | 107 | 315 |
| 0.25 mole % (MAc)$_3$(OMe)$_5$sucrose | 108 | 313 |
| 0.10 mole % (MAc)$_3$(OMe)$_5$sucrose | 110 | 309 |
| 0.05 mole % (MAc)$_3$(OMe)$_5$sucrose | 111 | 292 |
| PMMA copolymer containing Octa-O-allylsucrose | | |
| 3.00 mole % Octa-O-allylsucrose | 94 | 354 |
| 2.50 mole % Octa-O-allylsucrose | 97 | 353 |
| 2.00 mole % Octa-O-allylsucrose | 98 | 354 |
| 1.50 mole % Octa-O-allylsucrose | 100 | 353 |
| 1.00 mole % Octa-O-allylsucrose | 101 | 354 |
| 0.50 mole % Octa-O-allylsucrose | 107 | 338 |
| 0.10 mole % Octa-O-allylsucrose | 118 | 334 |
| PMMA copolymer containing Octa-O-crotylsucrose | | |
| 1.00 mole % Octa-O-crotylsucrose | 110 | 331 |
| PMMA copolymer containing Octa-O-methylsucrose | | |
| 1.00 mole % Octa-O-methylsucrose | 98 | 309 |
| PMMA copolymer containing Penta-O-methylsucrose triacetate | | |
| 1.00 mole % Penta-O-methylsucrose triacetate | 93 | 283 |
| PMMA copolymer containing Sucrose Octaacetate* | | |
| 1.00 mole % Sucrose Octaacetate | 95 | 278 |

TABLE 3-continued

Glass Transition Temperature and Thermal Degradation Temperatures of PMMA and Copolymers Containing Various Mole Percentages of TMPTMA and Sucrose-Based Additives

| Mole % Crosslinker | Glass Transitions Temperature (°C.) | Thermal Degradation Temperature (°C.) |
|---|---|---|
| PMMA copolymer containing Diacetate hexaisobutyrate sucrose* | | |
| 1.00 mole % Diacetate hexaisobutyrate sucrose | 92 | 247 |

1 - *product of Eastman Kodak used as a viscosity modified
2 - TMPTMA = trimethylolpropane trimethacrylate
3 - (MAc)$_3$(OMe)$_5$sucrose = penta-O-methylsucrose trimethacrylate
4 - All the samples were bulk copolymerized except copolymers containing 1 mole % TMPTMA and (MAc)$_3$(OMe)$_5$sucrose
5 - All polymers regardless of their mode of polymerization were heated to 140° C. for 12 hours before thermal analysis
6 - Each temperature was determined four times

Example 5
Polymer Aging

The polymer samples were dried in an oven at about 140° C. for about 12 hours. The dry polymer samples were weighed in crucibles (of known weight) and placed in an oven (under a fume canopy) set at about 200° C. After every 3 hours up to 24 hours, the polymer samples were removed from the oven, cooled, and reweighed in the crucibles. Thereafter, the samples were weighed once every 24 hours for up to the duration of each study (9 or 17 days as deemed necessary).

The results of the aging studies on PMMA and copolymers containing TMPTMA, penta-O-methylsucrose trimethacrylate, and octa-O-allylsucrose, for durations of 24 hours and 8.5 days are shown in Tables 4 and 5. Because PMMA copolymers containing octa-O-allylsucrose were so thermally stable, the polymer aging study was extended for 17 days to show a degradation profile (see Table 6). These studies showed the percent remaining weight of the copolymer as a sample degraded when heated at 200° C. for a given length of time.

From Tables 4, 5 and 6 the following results can be seen:

(1) Pure PMMA degrades rapidly when heated at 200° C. (e.g., after 24 hours, 7 days and 17 days at 200° C., the percent remaining weight rapidly declined to 14%, 4%, and 1% of the original mass).

(2) The same can be said of PMMA copolymers containing various mole percentages of TMPTMA (they also degraded to 15% and 6% of their original masses at 200° C. after 24 hours and 8.5 days).

(3) PMMA copolymers containing various mole percentages of penta-O-methylsucrose trimethacrylate possessed unusual thermal stability. Never before has a methyl methacrylate copolymer been shown to survive at 200° C., retaining 85% of its original weight after 24 hours, and 67% of its original weight after 8 days at 200° C.

(4) PMMA copolymers containing octa-O-allylsucrose possessed exceptional thermal stability. It can clearly be seen from Table 6 that up to 70% of the original mass of the copolymer was retained on day 17 at 200° C.

TABLE 4

Percentage of Remaining Weight Versus Degradation Time at 200° C. for PMMA and PMMA Copolymers Containing Various Mole Percentages of TMPTMA, (MAc)$_3$(OMe)$_5$Sucrose or Octa-O-allylsucrose for 24 h

| | Time (h) | | | | | | | |
|---|---|---|---|---|---|---|---|---|
| Mole % Crosslinker | 3 | 6 | 9 | 12 | 15 | 18 | 21 | 24 |
| Pure PMMA | | | | | | | | |
| 0 | 78.11 | 59.31 | 45.54 | 34.90 | 28.57 | 22.47 | 17.83 | 14.12 |
| PMMA Copolymer Containing TMPTMA | | | | | | | | |
| 1.00 | 90.64 | 68.75 | 48.61 | 38.87 | 30.25 | 24.50 | 18.69 | 15.63 |
| 0.75 | 84.75 | 59.15 | 45.09 | 36.56 | 30.01 | 24.23 | 19.91 | 16.95 |
| 0.50 | 77.66 | 53.81 | 41.37 | 31.59 | 24.81 | 18.92 | 15.12 | 13.02 |
| 0.25 | 80.50 | 60.31 | 47.36 | 36.03 | 27.90 | 21.00 | 16.87 | 13.78 |
| 0.10 | 81.41 | 65.89 | 47.07 | 35.05 | 25.69 | 19.75 | 15.43 | 13.41 |
| 0.05 | 77.56 | 61.17 | 44.73 | 34.21 | 24.23 | 18.30 | 14.64 | 12.58 |
| PMMA Copolymer Containing (MAc)$_3$ (OMe)$_5$Sucrose | | | | | | | | |
| 1.00 | 91.58 | 89.76 | 88.69 | 87.84 | 87.16 | 86.70 | 85.85 | 85.43 |
| 0.75 | 90.61 | 89.09 | 88.16 | 87.64 | 87.31 | 87.13 | 86.65 | 86.54 |
| 0.50 | 91.75 | 90.16 | 89.30 | 88.57 | 88.17 | 87.81 | 87.11 | 86.80 |
| 0.25 | 91.80 | 89.91 | 88.99 | 88.31 | 87.38 | 86.88 | 84.59 | 80.79 |
| 0.10 | 89.42 | 87.49 | 86.87 | 86.01 | 85.81 | 79.84 | 59.95 | 43.82 |
| 0.05 | 88.42 | 81.15 | 65.48 | 47.05 | 35.46 | 26.44 | 19.31 | 15.50 |

TABLE 4-continued

Percentage of Remaining Weight Versus Degradation Time at 200° C. for PMMA and PMMA Copolymers Containing Various Mole Percentages of TMPTMA, $(MAc)_3(OMe)_5$Sucrose or Octa-O-allylsucrose for 24 h

| Mole % Crosslinker | Time (h) | | | | | | | |
|---|---|---|---|---|---|---|---|---|
| | 3 | 6 | 9 | 12 | 15 | 18 | 21 | 24 |
| PMMA Copolymer Containing Octa-O-allylsucrose | | | | | | | | |
| 3.00 | 92.51 | 90.96 | 89.73 | 89.05 | 88.15 | 87.74 | 87.41 | 87.07 |
| 2.50 | 93.96 | 92.80 | 91.72 | 91.03 | 90.34 | 89.99 | 89.55 | 89.21 |
| 2.00 | 93.91 | 92.78 | 91.64 | 90.98 | 90.24 | 89.70 | 89.43 | 88.97 |
| 1.50 | 93.73 | 92.50 | 90.98 | 90.21 | 89.23 | 88.62 | 88.30 | 87.74 |
| 1.00 | 94.19 | 92.99 | 91.98 | 91.27 | 90.48 | 90.11 | 89.50 | 89.03 |
| 0.50 | 91.40 | 88.29 | 85.81 | 84.32 | 82.82 | 81.68 | 80.47 | 79.28 |
| 0.10 | 83.14 | 72.63 | 62.23 | 55.24 | 48.37 | 43.41 | 39.14 | 34.90 |

TABLE 5

Percentage of Remaining Weight Versus Degradation Time at 200° C. for PMMA and PMMA Copolymers Containing Various Mole Percentages of TMPTMA, $(MAc)_3(OMe)_5$Sucrose or Octa-O-allylsucrose for 8.5 Days

| Mole % Crosslinker | Time (days) | | | | | | | |
|---|---|---|---|---|---|---|---|---|
| | 1.5 | 2.5 | 3.5 | 4.5 | 5.5 | 6.5 | 7.5 | 8.5 |
| Pure PMMA | | | | | | | | |
| 0 | 8.30 | 6.80 | 5.94 | 5.54 | 5.12 | 4.81 | 4.51 | 4.21 |
| PMMA Copolymer Containing TMPTMA | | | | | | | | |
| 1.00 | 10.71 | 9.22 | 8.55 | 7.93 | 7.38 | 6.95 | 6.68 | 6.23 |
| 0.75 | 12.65 | 11.16 | 10.20 | 9.46 | 8.86 | 8.45 | 7.99 | 7.67 |
| 0.50 | 11.07 | 9.69 | 8.84 | 8.35 | 7.99 | 7.48 | 7.12 | 6.74 |
| 0.25 | 10.70 | 9.50 | 8.68 | 8.11 | 7.58 | 7.25 | 6.85 | 6.48 |
| 0.10 | 10.50 | 9.15 | 8.32 | 7.57 | 6.72 | 6.03 | 5.46 | 5.01 |
| 0.05 | 10.34 | 8.95 | 8.15 | 7.51 | 6.71 | 6.18 | 5.68 | 5.27 |
| PMMA Copolymer Containing $(MAc)_3(OMe)_5$Sucrose | | | | | | | | |
| 1.00 | 82.61 | 80.03 | 77.74 | 75.43 | 73.17 | 70.79 | 68.81 | 67.19 |
| 0.75 | 85.08 | 54.08 | 35.56 | 24.22 | 20.44 | 18.35 | 16.90 | 15.88 |
| 0.50 | 82.32 | 73.13 | 65.34 | 59.77 | 54.80 | 50.81 | 47.85 | 45.24 |
| 0.25 | 69.25 | 49.32 | 38.60 | 29.86 | 25.24 | 22.15 | 20.41 | 18.85 |
| 0.10 | 14.21 | 10.59 | 9.74 | 8.85 | 7.96 | 7.26 | 6.65 | 6.25 |
| 0.05 | 11.70 | 10.42 | 9.65 | 8.83 | 8.03 | 7.29 | 6.71 | 6.25 |
| PMMA Copolymer Containing Octa-O-allylsucrose | | | | | | | | |
| 3.00 | 83.98 | 81.92 | 80.07 | 78.84 | 77.46 | 76.19 | 74.56 | 73.72 |
| 2.50 | 86.82 | 85.15 | 83.85 | 82.78 | 81.44 | 80.41 | 79.12 | 78.06 |
| 2.00 | 86.17 | 83.37 | 81.16 | 79.72 | 78.29 | 76.59 | 74.71 | 73.24 |
| 1.50 | 83.76 | 80.51 | 77.76 | 75.35 | 73.73 | 71.94 | 69.55 | 67.63 |
| 1.00 | 85.00 | 81.68 | 79.57 | 76.77 | 74.48 | 72.52 | 70.49 | 68.73 |
| 0.50 | 73.28 | 67.98 | 62.14 | 58.15 | 54.68 | 51.75 | 49.00 | 46.75 |

TABLE 6

Percentage of Remaining Weight Versus Degradation Time at 200° C. for PMMA and PMMA Copolymers Containing Various Mole Percentages of Octa-O-allylsucrose for 17 Days

| Mole % Crosslinker | Time (days) | | | | | | | |
|---|---|---|---|---|---|---|---|---|
| | 10 | 11 | 12 | 13 | 14 | 15 | 16 | 17 |
| Pure PMMA | | | | | | | | |
| 0 | 3.16 | 2.26 | 2.21 | 1.86 | 1.69 | 1.45 | 1.37 | 1.28 |
| PMMA Copolymer Containing Octa-O-allylsucrose | | | | | | | | |
| 3.00 | 72.42 | 71.31 | 70.63 | 69.55 | 68.47 | 67.50 | 66.74 | 66.07 |
| 2.50 | 76.86 | 75.65 | 74.91 | 73.94 | 72.88 | 71.91 | 71.15 | 70.42 |
| 2.00 | 71.62 | 70.03 | 69.00 | 67.66 | 65.98 | 64.60 | 63.42 | 62.16 |
| 1.50 | 65.56 | 63.59 | 62.16 | 60.48 | 58.75 | 57.51 | 56.21 | 54.78 |
| 1.00 | 66.84 | 64.82 | 63.50 | 61.61 | 59.96 | 58.80 | 56.64 | 55.18 |
| 0.50 | 44.27 | 41.88 | 40.67 | 39.26 | 38.11 | 36.63 | 35.47 | 34.03 |
| 0.10 | 9.57 | 8.79 | 8.51 | 8.13 | 7.47 | 7.06 | 6.75 | 6.46 |

Example 6

Another aging study was conducted identical to Example 5 except that the polymer samples were dried in the oven at about 110° C. for 2 days. The results are in Tables 7 and 8.

Tables 7 and 8 show isothermal aging studies on PMMA and copolymers containing TMPTMA, penta-O-methylsucrose trimethacrylate, octa-O-allylsucrose, sucrose octaacetate, sucrose diacetate hexaisobutyrate, penta-O-methylsucrose triacetate, and octa-O-crotylsucrose, for durations of 1 and 8.5 days, respectively. These studies show the percent remaining weight of the copolymers as they degraded at 200° C. From Tables 7 and 8 we can see the following:

(1) Pure PMMA degrades rapidly when heated at 200° C.; the percent of remaining weight dropped to 14% and 4% after 1 and 8.5 days respectively;

(2) PMMA containing various mole percentages TMPTMA acted similarly; they, too, degraded to about 17% and 6% of their original masses after 1 and 8.5 days;

(3) PMMA samples containing various mole percentages of crosslinker appeared to be thermally stable. Samples containing 0.5 to 1 mole % penta-O-methylsucrose trimethacrylate retained about 91% of their original weights for 24 h. The one mole % sample retained 72% of its original weight for 8.5 days;

(4) Similarly, PMMA samples containing the crosslinker octa-O-allylsucrose ($\leq 1$ mole %) retained 91% and 72% of their original weights after 1 and 8.5 days;

(5) PMMA containing octa-O-crotylsucrose retained 94% and 78% of its original weight after 1 and 8.5 days;

(6) PMMA samples containing sucrose octaacetate, diacetate hexaisobutyrate sucrose, and penta-O-methylsucrose triacetate all showed reduced stability towards isothermal aging when compared with PMMA containing penta-O-methylsucrose trimethacrylate, octa-O-allylsucrose and octa-O-crotylsucrose, but all showed higher thermal stability than PMMA homopolymers (commercial or laboratory prepared) and copolymers containing TMPTMA;

(7) PMMA copolymers containing diallyl ether also degraded rapidly. The one mole % sample degraded with 24.6 and 12.6% of its weight remaining after 1 and 8.5 days, respectively, and the two mole % sample degraded to 36.2 and 15.3% under the same conditions.

TABLE 7

Percentage of Remaining Weight Versus Degradation Time (up to 24h) at 200° C. for PMMA and PMMA Containing Various Mole Percentages of TMPTMA and Sucrose-Based Monomers and Additives

| Time (h) Mole % Comonomer or Additive \|wt %\| | (Standard Deviation) | | | | | | | |
|---|---|---|---|---|---|---|---|---|
| | 3 | 6 | 9 | 12 | 15 | 18 | 21 | 24 |
| Pure PMMA | | | | | | | | |
| 0 | 78.1 (1.7) | 59.3 (1.9) | 45.5 (0.1) | 34.9 (0.6) | 28.6 (0.7) | 22.5 (0.2) | 17.8 (0.5) | 14.1 (0.1) |
| PMMA Containing TMPTMA | | | | | | | | |
| 1.00\|3.30\| | 96.1 (2.0) | 72.9 (5.9) | 51.5 (4.5) | 41.2 (4.2) | 32.1 (2.0) | 26.9 (1.4) | 19.8 (1.5) | 16.6 (0.5) |
| 0.75\|2.67\| | 89.8 (6.2) | 62.7 (3.0) | 47.8 (6.3) | 38.8 (5.1) | 31.8 (4.3) | 25.7 (2.1) | 21.1 (2.4) | 17.0 (1.0) |

TABLE 7-continued

Percentage of Remaining Weight Versus Degradation Time (up to 24h) at 200° C. for PMMA and PMMA Containing Various Mole Percentages of TMPTMA and Sucrose-Based Monomers and Additives

| Time (h) Mole % Comonomer or Additive [wt %] | 3 | 6 | 9 | 12 (Standard Deviation) | 15 | 18 | 21 | 24 |
|---|---|---|---|---|---|---|---|---|
| 0.50[1.74] | 82.3 (2.8) | 57.0 (1.5) | 43.9 (1.1) | 33.5 (2.5) | 26.3 (3.0) | 20.1 (2.5) | 16.0 (2.3) | 13.8 (2.0) |
| 0.25[0.84] | 85.3 (5.7) | 63.9 (6.4) | 50.2 (6.4) | 38.2 (3.9) | 29.6 (4.8) | 22.3 (4.1) | 17.9 (4.6) | 14.6 (2.0) |
| 0.10[0.34] | 86.3 (12.8) | 69.8 (25.2) | 49.9 (21.2) | 37.2 (15.0) | 27.2 (10.3) | 20.9 (7.2) | 16.4 (4.6) | 14.2 (3.1) |
| 0.05[0.17] | 82.2 (17.6) | 64.8 (21.6) | 47.4 (17.6) | 36.3 (13.1) | 25.7 (9.4) | 19.4 (5.0) | 15.3 (3.5) | 13.3 (1.9) |
| PMMA Containing Diallyl Ether | | | | | | | | |
| 2.00[1.96] | 89.3 (1.3) | 77.7 (0.3) | 69.3 (0.8) | 60.8 (1.1) | 51.7 (0.5) | 44.8 (1.8) | 39.0 (1.6) | 36.2 (1.4) |
| 1.00[0.98] | 88.3 (0.7) | 77.6 (0.5) | 66.8 (1.5) | 56.5 (1.1) | 38.9 (2.8) | 31.9 (1.5) | 26.6 (1.5) | 24.6 (1.7) |
| PMMA Containing penta-O-methyl-sucrose trimethacrylate | | | | | | | | |
| 1.00[5.85] | 98.0 (0.4) | 96.0 (0.3) | 94.9 (0.3) | 94.0 (0.3) | 93.3 (0.4) | 92.8 (0.4) | 91.9 (0.5) | 91.4 (0.5) |
| 0.75[4.44] | 97.0 (0.2) | 95.3 (0.4) | 94.3 (0.3) | 93.8 (0.4) | 93.4 (0.3) | 93.2 (0.3) | 92.7 (0.4) | 92.6 (0.4) |
| 0.50[3.00] | 98.1 (0.1) | 96.5 (0.1) | 95.6 (0.2) | 94.8 (0.2) | 94.3 (0.0) | 94.0 (0.1) | 93.2 (0.2) | 92.9 (0.3) |
| 0.25[1.52] | 98.2 (0.3) | 96.2 (0.0) | 95.2 (0.1) | 94.5 (0.0) | 93.5 (1.1) | 93.0 (1.5) | 90.5 (3.9) | 86.4 (9.3) |
| 0.10[0.62] | 95.7 (0.4) | 93.6 (0.2) | 93.0 (0.2) | 92.0 (0.1) | 91.8 (0.2) | 85.4 (0.2) | 64.1 (0.1) | 46.9 (2.8) |
| 0.05[0.31] | 94.6 (0.7) | 86.8 (9.3) | 70.1 (8.6) | 50.3 (6.5) | 37.9 (9.8) | 28.3 (7.2) | 20.7 (4.5) | 16.6 (1.6) |
| PMMA Containing octa-O-allylsucrose | | | | | | | | |
| 3.00[16.98] | 96.2 (1.4) | 94.6 (1.3) | 93.3 (1.3) | 92.6 (1.4) | 91.7 (1.5) | 91.2 (1.6) | 90.9 (1.6) | 90.6 (1.8) |
| 2.50[14.50] | 97.7 (0.5) | 96.5 (0.2) | 95.4 (0.4) | 94.7 (0.3) | 94.0 (0.4) | 93.6 (0.3) | 93.1 (0.2) | 92.8 (0.2) |
| 2.00[11.89] | 97.7 (0.1) | 96.5 (0.2) | 95.3 (0.3) | 94.6 (0.3) | 93.8 (0.5) | 93.3 (0.3) | 93.0 (0.2) | 92.5 (0.2) |
| 1.50[9.15] | 97.7 (0.1) | 96.2 (0.3) | 94.6 (0.5) | 93.8 (0.2) | 92.8 (0.3) | 92.2 (0.1) | 91.8 (0.1) | 91.2 (0.2) |
| 1.00[6.26] | 98.0 (0.4) | 96.7 (0.4) | 95.7 (0.2) | 94.9 (0.4) | 94.1 (0.4) | 93.7 (0.1) | 93.1 (0.6) | 92.6 (0.6) |
| 0.50[3.22] | 95.1 (0.5) | 91.8 (0.1) | 89.2 (0.1) | 87.7 (0.5) | 86.1 (0.2) | 84.9 (0.6) | 83.7 (0.4) | 82.5 (0.3) |
| 0.10[0.66] | 86.5 (1.1) | 75.5 (2.2) | 64.7 (2.1) | 57.4 (1.2) | 50.3 (1.9) | 45.1 (2.9) | 40.7 (1.4) | 36.3 (1.8) |
| PMMA Containing octa-O-crotylsucrose | | | | | | | | |
| 1.00[7.24] | 93.8 (1.0) | 92.8 (1.0) | 92.4 (0.9) | 92.0 (1.0) | 91.9 (1.0) | 91.8 (1.0) | 91.4 (1.1) | 90.9 (1.3) |
| PMMA Containing Penta-O-methyl-sucrose Triacetate | | | | | | | | |
| 1.00[5.16] | 94.4 (3.3) | 83.6 (12.1) | 75.0 (15.5) | 68.2 (15.1) | 63.2 (14.7) | 58.4 (13.7) | 54.1 (12.4) | 50.0 (11.9) |
| PMMA Containing Sucrose Octaacetate | | | | | | | | |
| 1.00[6.41] | 71.6 (11.7) | 48.8 (8.0) | 37.7 (7.3) | 29.1 (4.6) | 24.7 (2.7) | 22.1 (1.80) | 20.3 (1.3) | 18.9 (0.9) |
| PMMA Containing Diacetate Hexa-isobutyrate Sucrose | | | | | | | | |
| 1.00[7.87] | 56.2 (6.7) | 38.4 (4.6) | 30.7 (4.5) | 25.7 (4.2) | 23.3 (3.6) | 21.6 (2.8) | 20.5 (2.3) | 19.4 (2.2) |

TABLE 8

Percentage of Remaining Weight Versus Degradation Time (1.5 to 8.5 days) at 200° C. for PMMA and PMMA Containing Various Mole Percentages of TMPTMA and Sucrose-Based Monomers and Additives

| Time (days) Mole % Comonomer or Additive [wt %] | 1.5 | 2.5 | 3.5 | 4.5 (Standard Deviation) | 5.5 | 6.5 | 7.5 | 8.5 |
|---|---|---|---|---|---|---|---|---|
| Pure PMMA | | | | | | | | |
| 0 | 8.3 (0.1) | 6.8 (0.2) | 5.9 (0.0) | 5.5 (0.2) | 5.1 (0.1) | 4.8 (0.2) | 4.5 (0.1) | 4.2 (0.2) |

TABLE 8-continued

Percentage of Remaining Weight Versus Degradation Time (1.5 to 8.5 days) at 200° C. for PMMA and PMMA Containing Various Mole Percentages of TMPTMA and Sucrose-Based Monomers and Additives

| Time (days)<br>Mole %<br>Comonomer<br>or Additive<br>[wt %] | 1.5 | 2.5 | 3.5 | 4.5 (Standard Deviation) | 5.5 | 6.5 | 7.5 | 8.5 |
|---|---|---|---|---|---|---|---|---|
| PMMA Containing TMPTMA | | | | | | | | |
| 1.00[3.30] | 11.4 (0.5) | 9.8 (0.3) | 9.1 (0.6) | 8.4 (0.4) | 7.8 (0.2) | 7.4 (0.0) | 7.1 (0.0) | 6.6 (0.0) |
| 0.75[2.67] | 13.4 (0.7) | 11.8 (0.1) | 10.8 (0.1) | 10.0 (0.3) | 9.4 (0.4) | 9.0 (0.5) | 8.5 (0.6) | 8.1 (0.6) |
| 0.50[1.74] | 11.7 (1.4) | 10.3 (1.2) | 9.4 (1.3) | 8.9 (1.2) | 8.5 (1.1) | 7.9 (1.0) | 7.5 (0.8) | 7.1 (0.6) |
| 0.25[0.84] | 11.3 (0.6) | 10.1 (0.1) | 9.2 (0.1) | 8.6 (0.3) | 8.0 (0.3) | 7.7 (0.3) | 7.3 (0.3) | 6.9 (0.2) |
| 0.10[0.34] | 11.1 (2.3) | 9.7 (2.1) | 8.8 (1.9) | 8.0 (1.3) | 7.1 (1.0) | 6.4 (0.8) | 5.8 (0.6) | 5.3 (0.5) |
| 0.05[0.17] | 11.0 (1.5) | 9.5 (0.9) | 8.6 (0.7) | 8.0 (0.4) | 7.1 (0.4) | 6.6 (0.1) | 6.0 (0.0) | 5.6 (0.2) |
| PMMA Containing Diallyl Ether | | | | | | | | |
| 2.00[1.96] | 26.8 (0.2) | 23.2 (0.1) | 20.8 (0.1) | 19.6 (0.0) | 18.2 (0.3) | 17.1 (0.6) | 16.2 (0.6) | 15.3 (0.5) |
| 1.00[0.98] | 20.0 (1.6) | 17.9 (1.2) | 16.5 (1.2) | 15.4 (1.3) | 14.5 (1.1) | 13.7 (1.1) | 13.2 (1.0) | 12.6 (1.2) |
| PMMA Containing penta-O-methyl-sucrose trimethacrylate | | | | | | | | |
| 1.00[5.85] | 88.4 (0.7) | 85.6 (1.9) | 83.2 (1.8) | 80.7 (2.4) | 78.3 (2.9) | 75.7 (3.2) | 73.6 (3.6) | 71.9 (3.8) |
| 0.75[4.44] | 91.0 (0.4) | 57.9 (11) | 38.0 (6.2) | 25.9 (1.2) | 21.9 (0.8) | 19.6 (1.4) | 18.1 (1.6) | 17.0 (1.1) |
| 0.50[3.00] | 88.1 (1.2) | 78.2 (5.8) | 69.9 (6.2) | 64.0 (5.6) | 58.6 (4.9) | 54.4 (4.8) | 51.2 (4.4) | 48.4 (4.2) |
| 0.25[1.52] | 74.1 (1.8) | 52.8 (2.2) | 41.3 (1.8) | 32.0 (1.5) | 27.0 (2.5) | 23.7 (2.2) | 21.8 (2.0) | 20.2 (1.8) |
| 0.10[0.62] | 15.2 (0.4) | 11.3 (0.2) | 10.4 (0.4) | 9.0 (0.7) | 8.5 (0.9) | 7.8 (0.8) | 7.1 (0.8) | 6.7 (0.8) |
| 0.05[0.31] | 12.5 (0.0) | 11.1 (0.5) | 10.3 (0.5) | 9.4 (0.3) | 8.6 (0.4) | 7.8 (0.5) | 7.2 (0.6) | 6.7 (0.5) |
| PMMA Containing octa-O-allylsucrose | | | | | | | | |
| 3.00[16.98] | 87.3 (2.2) | 85.2 (2.3) | 83.3 (2.5) | 82.0 (3.2) | 80.6 (3.4) | 79.2 (3.6) | 77.5 (3.8) | 76.7 (3.4) |
| 2.50[14.50] | 90.3 (0.6) | 88.6 (0.5) | 87.2 (0.5) | 86.1 (0.6) | 84.7 (0.9) | 83.6 (1.0) | 82.2 (1.0) | 81.2 (1.3) |
| 2.00[11.89] | 89.6 (0.3) | 86.7 (0.1) | 84.4 (0.4) | 82.9 (0.1) | 81.4 (0.1) | 79.7 (0.1) | 77.7 (0.1) | 76.2 (0.5) |
| 1.50[9.15] | 83.1 (0.9) | 82.7 (1.3) | 80.9 (1.9) | 78.4 (1.9) | 76.7 (1.5) | 74.8 (1.8) | 72.3 (1.6) | 70.3 (1.4) |
| 1.00[6.26] | 88.4 (1.1) | 84.9 (1.4) | 82.8 (2.8) | 79.4 (2.3) | 77.5 (2.3) | 75.4 (2.9) | 73.3 (2.7) | 71.5 (2.5) |
| 0.50[3.22] | 76.2 (0.1) | 70.7 (1.9) | 64.6 (2.0) | 60.5 (1.1) | 56.9 (0.1) | 53.8 (0.1) | 51.0 (1.1) | 48.6 (1.0) |
| 0.10[0.66] | 19.6 (0.6) | 16.7 (0.9) | 15.4 (0.6) | 14.3 (0.9) | 13.3 (1.2) | 12.3 (1.2) | 11.3 (1.1) | 10.7 (2.4) |
| PMMA Containing octa-O-crotylsucrose | | | | | | | | |
| 1.00[7.24] | 93.5 (0.2) | 90.8 (0.4) | 87.8 (1.2) | 84.9 (1.1) | 82.5 (1.1) | 80.7 (0.9) | 79.5 (1.0) | 78.2 (1.6) |
| PMMA Containing Penta-O-methyl-sucrose Triacetate | | | | | | | | |
| 1.00[5.16] | 40.9 (9.9) | 31.9 (6.5) | 27.5 (5.0) | 25.1 (4.1) | 23.2 (4.0) | 21.9 (4.0) | 19.5 (3.3) | 16.6 (3.5) |
| PMMA Containing Sucrose Octaacetate | | | | | | | | |
| 1.00[6.41] | 16.1 (0.4) | 13.3 (0.5) | 12.0 (0.6) | 10.9 (0.8) | 10.2 (0.6) | 9.6 (0.9) | 8.6 (0.8) | 7.6 (0.9) |
| PMMA Containing Sucrose Diacetate Hexaisobutyrate | | | | | | | | |
| 1.00[7.87] | 17.7 (1.6) | 15.5 (2.1) | 13.1 (1.5) | 12.2 (2.1) | 10.9 (2.1) | 10.5 (1.8) | 9.2 (1.7) | 7.9 (1.7) |

Example 7

In this experiment, the thermal degradation of crosslinked poly(methyl methacrylate) copolymers containing various mole percentages of either trimethylolpropane trimethacrylate (TMPTMA) or 1',6,6'-trimethacryloyl-2,3,3',4,4'-penta-O-methylsucrose [(MAc)$_3$(OMe)$_5$sucrose] as a crosslinking agent were compared.

Thermal gravimetric analyses were performed using the Shimadzu TGA-50 thermogravimetric analyzer. The temperature range for each thermal decomposition was 30° C. to 450° C., with a temperature increment rate of 10° C. per minute. Decompositions were conducted under an atmosphere of dry nitrogen gas, flowing at 20 ml per minute through the sample.

The purpose of these experiments was to determine and compare the decomposition temperatures of linear poly (methyl methacrylate), and crosslinked poly(methyl methacrylate) copolymers containing various percentages of either trimethylolpropane trimethacrylate (TMPTMA) or 1',6,6'-trimethacryloyl-2,3,3',4,4'-penta-O-methylsucrose [(MAc)$_3$(OMe)$_5$sucrose] as crosslinking agents. All samples were oven dried at 100° C. overnight prior to use in the experiment. Percent decomposition equals percent weight loss in these experiments, over a temperature range of 30°–450° C. The results of these experiments are shown in Table 9.

Table 10 shows the decomposition temperatures of individual sucrose-based compounds and PMMA containing one mole % of each monomer or additive.

TABLE 9

THERMAL DEGRADATION TEMPERATURES (°C.) FOR CROSSLINKED POLY(METHYL METHACRYLATE)[1,2,3] COPOLYMERS CONTAINING VARIOUS PERCENTAGES OF EITHER TRIMETHYLOLPROPANE TRIMETHACRYLATE (TMPTMA) OR 1',6,6'-TRIMETHACRYLOYL-2,3,3',4,4'-PENTA-O-METHYLSUCROSE [(MAc)₃(OMe)₅sucrose]

| Mol % Crosslinker | TMPTMA[5] (°C.) | (MAc)₃(OMe)₅sucrose (°C.) | ΔT (°C.) |
|---|---|---|---|
| 1.0 | (285) | (320) | (35) |
| 0.75 | (278) | (316) | (38) |
| 0.50 | (286) | (317) | (31) |
| 0.25 | (289) | (316) | (27) |
| 0.10 | (275) | (306) | (31) |
| 0.05[4] | (281) | (294) | (13) |

[1]Thermal degradation temperature of linear poly(methyl methacrylate) = 280° C.
[2]Average increase in decomposition temperatures = 35 + 38 + 31 + 27 + 31/5 = 32.5° C. Data for 0.05% crosslinker concentration are excluded (since this is a negligible amount of crosslinker it does not affect thermal stability).
[3]Polymers containing 1',6,6'-trimethacryloyl-2,3,3',4,4'-penta-O-methylsucrose [(MAc)₃(OMe)₅sucrose] degrade at temperatures 30° C. higher and are thermally more stable than crosslinked methyl methacrylate copolymers containing various percentages of trimethylolpropane trimethacrylate (TMPTMA).
[4]Even when there is a negligible amount of sucrose crosslinker (0.05%), there is an increase in the degradation temperature of the polymer compared with linear or crosslinked poly(methyl methacrylate) containing TMPTMA.
[5]All crosslinked polymers containing trimethylopropane trimethacrylate degrade at about the same temperatures as uncrosslinked poly(methyl methacrylate).

The data show that uncrosslinked poly(methyl methacrylate) degrades at 280° C. All crosslinked polymers containing TMPTMA as the crosslinking agent decompose between 275°–290° C. It appears that there is no increase in the thermal stability of crosslinked poly(methyl methacrylate) containing TMPTMA as the crosslinking agent.

When crosslinked poly(methyl methacrylate) copolymers containing [(MAc)₃(OMe)₅sucrose] were thermally degraded, a 30° C. rise in the degradation temperature for all copolymers was observed. This suggests that crosslinked methyl methacrylate copolymers with [(MAc)₃(OMe)₅sucrose] as the crosslinking agent are more thermally stable than those copolymers containing TMPTMA.

TABLE 10

Decomposition Temperatures of Individual Sucrose-Based Compounds as Well as PMMA Containing 1 Mole % of Each Monomer or Additive

| Monomer or Additive | Decomposition Temperature of Individual Compound (°C.) | Decomposition Temperature of Polymer Containing 1 Mole % of Each Compound (°C.) |
|---|---|---|
| (OAc)₈sucrose | 287 | 278 |
| (OAc)₂(iBu)₆sucrose | 278 | 247 |

TABLE 10-continued

Decomposition Temperatures of Individual Sucrose-Based Compounds as Well as PMMA Containing 1 Mole % of Each Monomer or Additive

| Monomer or Additive | Decomposition Temperature of Individual Compound (°C.) | Decomposition Temperature of Polymer Containing 1 Mole % of Each Compound (°C.) |
|---|---|---|
| (OMe)₅sucrose(OAc)₃ | 256 | 283 |
| (OMe)₅sucrose(MAc)₃ | 308 | 320 |
| (OAllyl)₈sucrose | 310 | 354 |
| (OCrotyl)₈sucrose | 272 | 322 |

As can be seen by the examples, the present inventors have discovered two stabilizing agents that are crosslinkers, namely octa-O-allylsucrose and 1',6,6'-trimethacryloyl-2,3,3',4,4'-penta-O-methylsucrose that provide unprecedented thermal stability to the methyl methacrylate copolymers containing them. In addition, the present inventors have discovered non-crosslinking additives octa-O-methylsucrose and octa-O-crotylsucrose which provide more thermal stability to any known PMMA and styrene-based materials than the commercially used crosslinker trimethylolpropane trimethacrylate and perhaps the stabilizer di-tert-dodecyl disulfide.

Example 8

The thermal degradation profiles of pure polystyrene and polystyrene containing one mole percent octa-O-allyl sucrose were obtained as with the PMMA examples described above.

Figure 4:
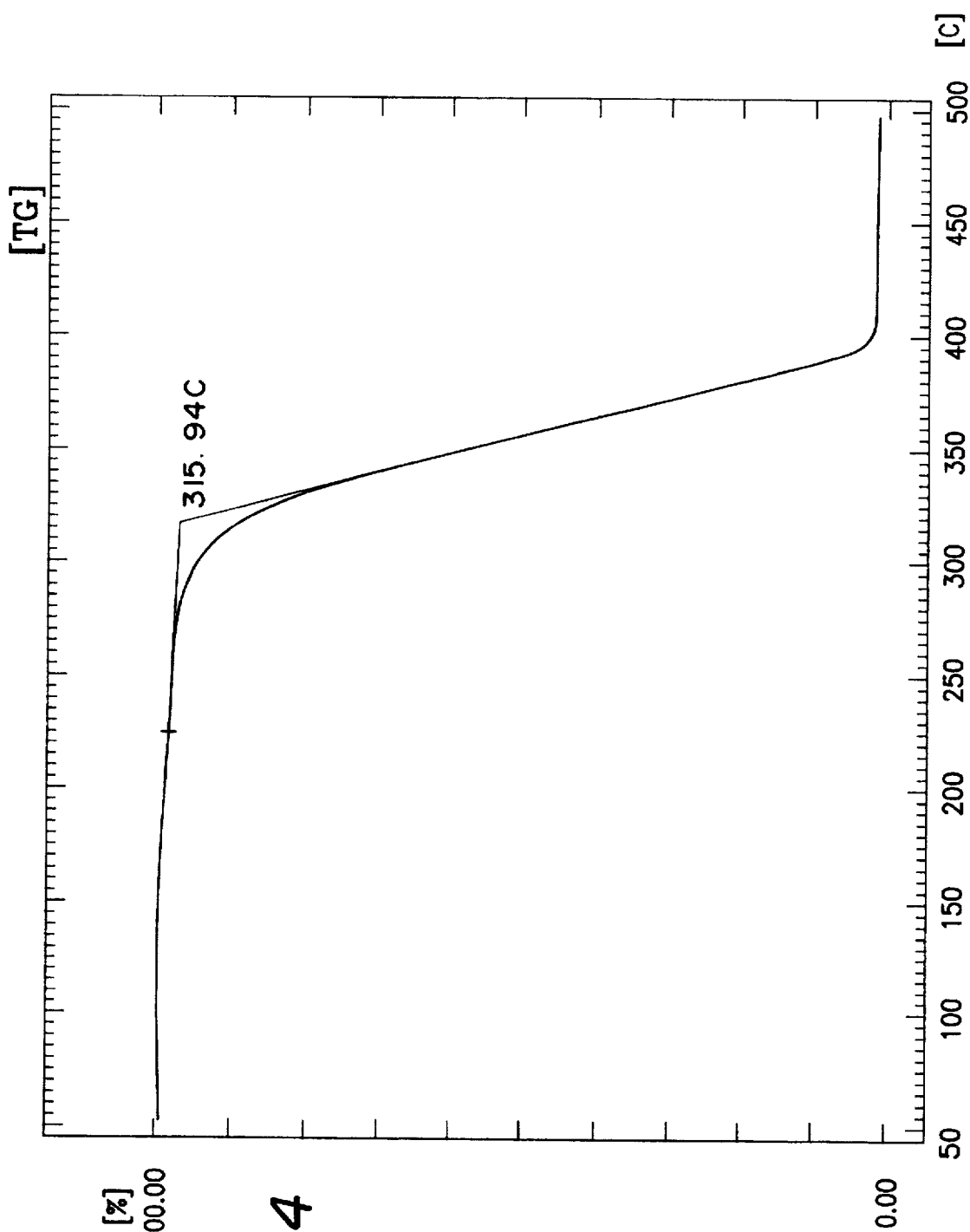
FIG. 4 represents the thermal degradation profile of pure polystyrene.
Figure 5:
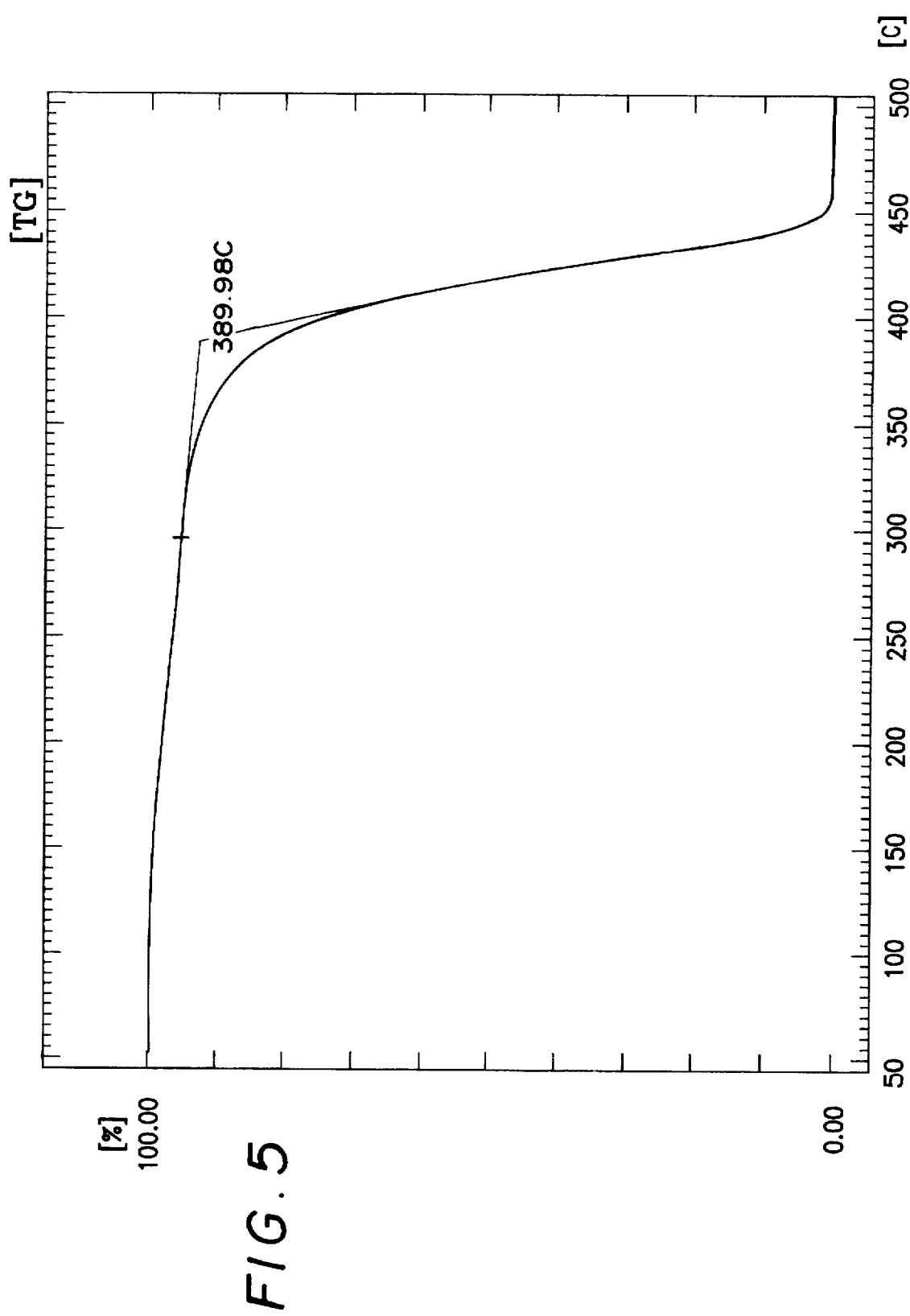
FIG. 5 represents the thermal degradation profile of polystyrene containing one mole percent octa-O-allyl sucrose.

The results are shown in FIGS. 4 and 5.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

We claim:

1. A method for producing polymers comprising an additive compound, the addition of which results in polymers exhibiting enhanced thermal stability relative to polymers lacking said additive compound, which comprises polymerizing a mixture comprising:

(a) an additive compound comprising a benzylether derivative of sucrose; and (b) one or more monomers selected from the group consisting of methacrylate ester monomers, acrylamide monomers, acrylate ester monomers and styrene monomers, in relative amounts sufficient to produce a polymer exhibiting enhanced thermal stability relative to a polymer which lacks said additive compound, and wherein said additive compound does not participate in the polymerization reaction.

2. The method of claim 1 wherein the benzylether derivative of sucrose comprises long chain hydrocarbon substituents at one or more of positions 2 to 6 of the aromatic ring.

3. The method of claim 2 wherein the long chain substituents comprise from 3 to 20 carbon atoms.

4. The polymer produced by the method of claim 3.

5. The polymer produced by the method of claim 2.

6. The method of claim 1 wherein the monomers of (b) are selected from the group consisting of methyl methacrylate, methyl acrylate, styrene, acrylamide and acrylonitrile.

7. The polymer produced by the method of claim 6.

8. The polymer produced by the method of claim 1.

9. The method of claim 1, wherein the benzylether sucrose is octa-O-benzyl sucrose.

* * * * *